US010166270B2

(12) United States Patent
Thomas et al.

(10) Patent No.: US 10,166,270 B2
(45) Date of Patent: *Jan. 1, 2019

(54) COMPOSITION AND METHOD FOR AFFECTING CYTOKINES AND NF-κB

(71) Applicant: Zivo Bioscience, Inc., Keego Harbor, MI (US)

(72) Inventors: Tiffany Thomas, Scottsdale, AZ (US); Fazlul Sarkar, Plymouth, MI (US); Denis Callewaert, Metamora, MI (US); Andrew Dahl, Bloomfield Hills, MI (US); Enrique Martinez, Clinton Township, MI (US)

(73) Assignee: Zivo Bioscience, Inc., Keego Harbor, MI (US)

( * ) Notice: Subject to any disclaimer, the term of this patent is extended or adjusted under 35 U.S.C. 154(b) by 306 days.

This patent is subject to a terminal disclaimer.

(21) Appl. No.: 14/558,516

(22) Filed: Dec. 2, 2014

(65) Prior Publication Data

US 2015/0157688 A1 Jun. 11, 2015
US 2017/0360883 A9 Dec. 21, 2017

Related U.S. Application Data

(63) Continuation-in-part of application No. 13/841,739, filed on Mar. 15, 2013, now abandoned, which is a continuation-in-part of application No. 12/897,574, filed on Oct. 4, 2010, now Pat. No. 8,791,060, and a continuation-in-part of application No. 12/947,684, filed on Nov. 16, 2010, now abandoned, said application No. 12/897,574 is a continuation of application No. 11/606,676, filed on Nov. 30, 2006, now Pat. No. 7,807,622, which is a continuation-in-part of application No. PCT/US2005/013375, filed on Apr. 20, 2005, and a continuation-in-part of application No. PCT/US2006/015302, filed on Apr. 20, 2006.

(60) Provisional application No. 61/261,639, filed on Nov. 16, 2009, provisional application No. 60/741,774, filed on Dec. 2, 2005, provisional application No. 60/565,011, filed on Apr. 23, 2004, provisional application No. 60/719,025, filed on Sep. 21, 2005.

(51) Int. Cl.

| A61K 36/07 | (2006.01) |
| A61K 35/66 | (2015.01) |
| A61K 35/74 | (2015.01) |
| A61K 38/16 | (2006.01) |
| A61K 38/02 | (2006.01) |
| A61K 36/06 | (2006.01) |
| A61K 31/715 | (2006.01) |
| A61K 36/02 | (2006.01) |
| A61K 36/10 | (2006.01) |

(52) U.S. Cl.
CPC .......... *A61K 38/168* (2013.01); *A61K 31/715* (2013.01); *A61K 35/74* (2013.01); *A61K 36/02* (2013.01); *A61K 36/06* (2013.01); *A61K 36/10* (2013.01); *A61K 38/02* (2013.01); *A61K 38/164* (2013.01)

(58) Field of Classification Search
None
See application file for complete search history.

(56) References Cited

U.S. PATENT DOCUMENTS

| 4,012,504 A | 3/1977 | Eckols |
| 4,303,409 A | 12/1981 | Ogawa et al. |
| 4,471,055 A | 9/1984 | Opp |
| 4,822,612 A | 4/1989 | Shinpo |
| 5,726,063 A | 3/1998 | Gerard-Monnier et al. |
| 5,767,095 A | 6/1998 | Winget |
| 6,235,495 B1 | 5/2001 | Fu et al. |
| 6,374,874 B1 | 4/2002 | Payne |
| 6,461,607 B1 | 10/2002 | Farmer |
| 6,551,596 B2 | 4/2003 | Kralovec |
| 6,673,908 B1 | 1/2004 | Stanton |
| 6,733,751 B2 | 5/2004 | Farmer |
| 7,025,965 B1 | 4/2006 | Pieloch |
| 7,125,846 B2 | 10/2006 | Rojkjaer |
| 7,807,622 B2 * | 10/2010 | Thomas ............... A61K 31/715 514/4.8 |
| 8,586,053 B2 * | 11/2013 | Thomas ............... A61K 31/715 424/195.17 |

(Continued)

FOREIGN PATENT DOCUMENTS

| CA | 2564466 | 12/2005 |
| CA | 2485449 | 4/2006 |

(Continued)

OTHER PUBLICATIONS

PCT; International Search Report & Written Opinion dated Sep. 24, 2014 in Application No. PCT/US2014/42331.
Office Action dated Nov. 11, 2014 of Japanese Patent Application No. 2012-539974.
Hiroshi Fujita, "NF-KB: Regulation and Genetic engineering of Signal transduction of inflammation", Journal of Clinical and Experimental Medicine, 1999, 190(10),, pp. 913-916.
Eriko Okada et al., "Inflammatory bowel disease and Cytokine", separate volume of Journal of Clinical and Experimental Medicine, Oct. 2004, pp. 265-268.

(Continued)

*Primary Examiner* — Chris R Tate
*Assistant Examiner* — Randall Winston
(74) *Attorney, Agent, or Firm* — Snell & Wilmer LLP

(57) ABSTRACT

The present invention discloses a composition and method for effecting various cytokines and NF-κB by administering an effective amount of a phyto-percolate composition to an individual. In various exemplary embodiments, the composition is claimed to be useful for the effective treatment of inflammation, cancer, and/or various infections including HIV by regulation of various interleukins, such as IL-10 and IL-2, and of transcription factors including NF-κB.

19 Claims, 14 Drawing Sheets

(56) References Cited

U.S. PATENT DOCUMENTS

| | | | |
|---|---|---|---|
| 8,791,060 | B2 | 7/2014 | Thomas et al. |
| 9,486,005 | B2 | 11/2016 | Gupta et al. |
| 2002/0009479 | A1 | 1/2002 | Vardi et al. |
| 2002/0119164 | A1 | 8/2002 | Uchiyama et al. |
| 2003/0152587 | A1 | 8/2003 | Kralovec |
| 2005/0114920 | A1 | 5/2005 | Yusibov et al. |
| 2005/0229585 | A1 | 10/2005 | Webster |
| 2005/0260695 | A1 | 11/2005 | Flemming et al. |
| 2006/0101803 | A1 | 5/2006 | White |
| 2007/0010480 | A1 | 1/2007 | Rusing et al. |
| 2007/0207231 | A1* | 9/2007 | Thomas ............... A61K 31/715 424/780 |
| 2008/0089843 | A1 | 4/2008 | Pillarisetti et al. |
| 2008/0272232 | A1 | 11/2008 | Cagle et al. |
| 2008/0272615 | A1 | 11/2008 | McKnight et al. |
| 2009/0036372 | A1 | 2/2009 | Thomas et al. |
| 2009/0117216 | A9 | 5/2009 | Thomas et al. |
| 2011/0081319 | A1 | 4/2011 | Thomas et al. |
| 2011/0117122 | A1 | 5/2011 | Thomas et al. |
| 2012/0328598 | A1 | 12/2012 | Gupta et al. |
| 2013/0251698 | A1 | 9/2013 | Thomas et al. |
| 2016/0120970 | A1 | 5/2016 | Dahl et al. |
| 2017/0135391 | A1 | 5/2017 | Gupta et al. |
| 2018/0021392 | A1 | 1/2018 | Dahl et al. |

FOREIGN PATENT DOCUMENTS

| | | |
|---|---|---|
| CN | 102225127 | 10/2011 |
| EP | 1230927 | 8/2002 |
| EP | 1878877 | 1/2008 |
| EP | 1928247 | 10/2009 |
| EP | 2501390 | 9/2012 |
| JP | 0409040523 | 2/1997 |
| JP | 2009518312 | 5/2009 |
| JP | 2014006051 | 1/2014 |
| WO | WO2011060427 | 5/2001 |
| WO | WO2003028749 | 4/2003 |
| WO | WO2005112987 | 1/2005 |
| WO | 2006055217 | 5/2006 |
| WO | WO2006113925 | 10/2006 |
| WO | WO2007065024 | 6/2007 |
| WO | 2011016973 | 2/2011 |
| WO | WO2011103569 | 8/2011 |
| WO | WO2014201372 | 12/2014 |
| WO | WO2016133922 | 8/2016 |
| WO | WO2017142906 | 8/2017 |

OTHER PUBLICATIONS

Article titled "Research Indicates ProAlgazyme may Decrease Risk of Stroke or Heart Attack" dated Jan. 20, 2004 in SupplementQuality.com.
Office Action dated Feb. 26, 2015 for PCT No. US2006046320.
First Written Opinion dated Sep. 24, 2014 for PCT No. US201442331.
U.S. Appl. No. 12/897,574, filed Oct. 4, 2010, Composition and Use of Phyto-Percolate for Treatment of Disease.
U.S. Pat. No. 7,807,622, Oct. 5, 2010, Composition and Use of Phyto-Percolate for Treatment of Disease.
U.S. Pat. No. 8,586,053, Oct. 3, 2008, Composition and Use of Phyto-Percolate for Treatment of Disease.
U.S. Appl. No. 12/947,684, filed Nov. 16, 2010, Composition and Method for Affecting Cytokines and NF-KB.
U.S. Appl. No. 13/841,739, filed Mar. 15, 2013, Composition and Method for Affecting.
Advisory Action dated Mar. 6, 2009 in U.S. Appl. No. 11/606,676.
Final Office Action dated May 29, 2009 in U.S. Appl. No. 11/606,676.
Final Office Action dated Nov. 14, 2008 in U.S. Appl. No. 11/606,676.
Office Action dated Feb. 4, 2008 in U.S. Appl. No. 11/606,676.
Office Action dated Oct. 8, 2009 in U.S. Appl. No. 11/606,676.
Notice of Allowancec dated May 27, 2010 in U.S. Appl. No. 11/606,676.
Office action dated Oct. 22, 2012 in U.S. Appl. No. 12/067,735.
Requirement for Restriction dated Oct. 19, 2010 in U.S. Appl. No. 12/067,735.
Office Action dated Mar. 13, 2012 in U.S. Appl. No. 12/067,735.
Notice of Allowance dated Aug. 15, 2013 in U.S. Appl. No. 12/067,735.
Advisory Action dated Feb. 26, 2014 in U.S. Appl. No. 12/897,574.
Non-Final Office Action dated Jun. 24, 2013 in U.S. Appl. No. 12/897,574.
Final Office Action dated Nov. 13, 2013 in U.S. Appl. No. 12/897,574.
Notice of Allowance dated Apr. 8, 2014 in U.S. Appl. No. 12/897,574.
Final Office Action dated May 21, 2012 in U.S. Appl. No. 12/947,684.
Final Office Action dated Oct. 9, 2013 in U.S. Appl. No. 12/947,684.
Office Action dated Sep. 9, 2011 in U.S. Appl. No. 12/947,684.
Office Action dated Dec. 20, 2012 in U.S. Appl. No. 12/947,684.
Final Office Action dated Apr. 2, 2015 in U.S. Appl. No. 13/580,471.
Office Action dated Aug. 26, 2014 in U.S. Appl. No. 13/580,471.
Notice of Allowance dated Jun. 20, 2016 in U.S. Appl. No. 13/580,471.
Restriction Requirement dated Mar. 4, 2014 in U.S. Appl. No. 13/580,471.
Office Action dated Jun. 2, 2014 in U.S. Appl. No. 13/841,739.
Final Office Action dated May 1, 2017 in U.S. Appl. No. 14/898,091.
Office Action dated Jun. 28, 2016 in U.S. Appl. No. 14/898,091.
Office Action dated Oct. 3, 2016 in U.S. Appl. No. 14/898,091.
Restriction Requirement dated Dec. 8, 2012 in U.S. Appl. No. 13/397,360.
Office Action dated Jun. 19, 2014 in U.S. Appl. No. 13/397,360.
Australia: Examination Report dated Sep. 7, 2012 in AU2006320264.
Auustralia: Examination Report dated Apr. 11, 2014 in AU2013204257.
Canada: Examination Report dated Feb. 26, 2015 in CA2631773.
Canada: Examination Report dated Mar. 31, 2016 in CA2631773.
Canada: Examination Report dated Apr. 22, 2014 in CA2631773.
Canada: Examination Report dated May 24, 2014 in CA2631773.
Canada: Examination Report dated Mar. 23, 2017 in CA2780144.
Canada: Examination Report dated Oct. 15, 2016 in CA2780144.
EPO: Extended Search Report/Written Opinion dated Nov. 2, 2017 in EP20111745434.
EPO: Examination Report dated Mar. 22, 2012 in EP2006320264.
EPO: Examination Report dated Oct. 13, 2009 in EP2006320264.
EPO: Supplemental Search Report-Written Opinion dated Sep. 9, 2009 in EP2006758513.
EPO: Examination Report dated Mar. 31, 2016 in EP2010830908.
EPO: Extended Search Report dated Jun. 2, 2014 in EP20100830908.
Japan: Examination Report dated Aug. 7, 2012 in JP200854345.
PCT: Search Report and Written Opinion dated Jul. 29, 2011 in PCT/US2010056862.
PCT: IPRP dated May 22, 2012 in PCT/US2010056862.
PCT: IPRP dated Dec. 23, 2015 in PCT/US2014042331.
PCT: Written Opinion dated May 25, 2017 in PCT/US2017017906.
PCT: International Search Report dated May 25, 2017 in PCT/US2017017906.
PCT: Written Opinion dated Aug. 4, 2016 in PCT/US2016018105.
PCT: International Search Report dated Aug. 4, 2016 in PCT/US2016018105.
PCT: IPRP dated Aug. 22, 2017 in PCT/US2016018105.
PCT: Written Opinion dated Jun. 21, 2011 in PCT/US2011025713.
PCT: International Search Report dated Jun. 21, 2011 in PCT/US2011025713.
PCT: IPRP dated Aug. 28, 2012 in PCT/US2011025713.
PCT: Written Opinion of the International Searching Authority dated Dec. 6, 2009 for International Patent Application No. PCT/US2005/013375.
PCT: International Preliminary Report on Patentability dated Oct. 25, 2006 for International Patent Application No. PCT/US2005/013375.
PCT: Written Opinion of the International Searching Authority dated Mar. 22, 2007 for International Patent Application No. PCT/US2006/015302.
PCT: International Preliminary Report on Patentability dated Oct. 23, 2007 for International Patent Application No. PCT/US2006/015302.

(56) References Cited

OTHER PUBLICATIONS

PCT: International Search Report dated Jun. 4, 2008 for International Application No. PCT/US2006/046320.
PCT: International Search Report dated Feb. 23, 2012 for International Application No. PCT/US2011/44786.
PCT: Written Opinion dated Feb. 23, 2012 for International Application No. PCT/US2011/44786.
PCT: IPRP dated Jan. 29, 2013 for International Application No. PCT/US2011/44786.
Kim et al., "Purification and characterization of a fibrinolytic enzyme produced from *Bacillus* sp.strain CK 11-4 screened from Chungkook-Jang," Environ. Microbiology, vol. 62, No. 7, pp. 2482-2488, (Jul. 1996).
Noda et al., "A water-soluble antitumor glycoprotein from Chlorella vulgaris," Faculty of Pharmaceutical Sciences, Kyushu University, (Oct. 1996).
Oben et al., "The effects of ProAlgaZyme novel algae infusions on metabolic syndrome and markers of cardiovascular health," Lipids in Health and Disease, vol. 6, pp. 1-9, (2007).
Oben et al., "Lipids in Health and Disease: The effects of ProAlgaZyme novel algae infusion of metabolic syndrome and markers of cardiovascular health," BioMed Central, pp. 1-9, (Sep. 5, 2007).
Press Release entitled, "Western Glory Hole Inc. Enters Definitive Agreement with Health Enhancement Products In," Business Wire, (Oct. 30, 2003).
Sarkar et al., "Using Chemopreventive Agents to Enhance the Efficacy of Cancer Therapy," Cancer Research, vol. 66(7), pp. 3347-3350, (Apr. 1, 2006).
BioSuperfood-Algae/Spirulina for People. (2010). Optimum Choices. Retrieved Apr. 14, 2010 from http://www.optimumchoices.com/spirulina.htm as accessed Apr. 14, 2010.
Spirulina (2010). MedlinePlus U.S. National Library of Medicine and the National Institutes of Health. Retrieved Apr. 14, 2010 from http://www.nlm.nih.gov/medlineplus/druginfo/natural/patient-spirulina.html as accessed Apr. 14, 2010.
Scientific Paper Published Jun. 2012 in the Journal of Nutrition and Dietary Supplements by Smiti Gupta and group at WSU.
www.optimumchoices.com/spirulina.htm. (2007).
www.michaelkiriac.com, (Jan. 1, 2003).
www.nlm.nih.gov/medlineplus/druginfo/natural/patient-spirulina.html, (Aug. 1, 2006).
USPTO; Examiner Interview Summary Record dated Apr. 12, 2010 in U.S. Appl. No. 11/606,676.
USPTO; Final Office Action dated Nov. 3, 2008 in U.S. Appl. No. 11/587,266.
USPTO; Non-Final Office Action dated Feb. 4, 2008 in U.S. Appl. No. 11/587,266.
USPTO; Requirement for Restriction dated Jul. 20, 2011 in U.S. Appl. No. 12/067,735.
USPTO; Final Office Action dated Oct. 23, 2012 in U.S. Appl. No. 12/067,735.
USPTO; Notice of Allowance dated May 13, 2013 in U.S. Appl. No. 12/067,735.
USPTO; Advisory Action dated Aug. 7, 2015 in U.S. Appl. No. 13/804,471.
USPTO; Office Action dated Dec. 8, 2015 in U.S. Appl. No. 13/804,471.
USPTO; Final Office Action dated Jun. 5, 2018 in U.S. Appl. No. 14/898,091.
USPTO; Restriction Requirement dated Apr. 20, 2018 in U.S. Appl. No. 15/550,749.
USPTO; Restriction Requirement dated Aug. 6, 2018 in U.S. Appl. No. 15/330,830.
Canada: Examination Report dated May 16, 2017 in CA2631773.
Canada; Examination Report dated Jun. 27, 2018 in CA2631773.
EPO; Examination Report dated Nov. 20, 2009 in EP2006758513.
EPO; Examination Report dated Mar. 22, 2012 in EP2006758513.
EPO: Office Action dated Feb. 23, 2010 in EP2006838974.
EPO; Extended Search Report dated Aug. 10, 2018 in EP16752918.9.
Amaro et al., "Antimicrobial Activities of Microalgae: An Invited Review," Science Against Microbial Pathogens: Communicating Current Research and Technological Advances (Ed. Mendez-Vilas, A.), Formatex Research Center, Spain, ISBN-13: 978-84-939843-1-1, pp. 1272-1280, (2011).
Bhadury et al., "Exploitation of Marine Algae: Biogenic Compounds for Potential Antifouling Applications," Planta, (E-pub), vol. 219, No. 4, pp. 561-578, (Jun. 24, 2004).
Brewer et al., "Arteriosclerosis, Thrombosis, and Vascular Biology: Regulation of Plasma High-Density Lipoprotein Levels by the ABCA1 Transporter and the Emerging Role of High-Density Lipoprotein in the Treatment of Cardiovascular Disease," American Heart Association, vol. 24(24), pp. 1755-1760, (Aug. 19, 2004).
Kim, Young-Gon, and Moon-Seog Jun, "A Design of User Authentication System Using QR Code Identifying Method," Computer Sciences and Convergence Information Technology (ICCIT), 6th International Conference on IEEE, (Nov. 29-Dec. 1, 2011).
Mudimu et al., "Biotechnological Screening of Microalgal and Cyanobacterial Strains for Biogas Production and Antibacterial and Antifungal Effects," Metabolites, vol. 4, No. 2, pp. 373-393, (May 15, 2014).

\* cited by examiner

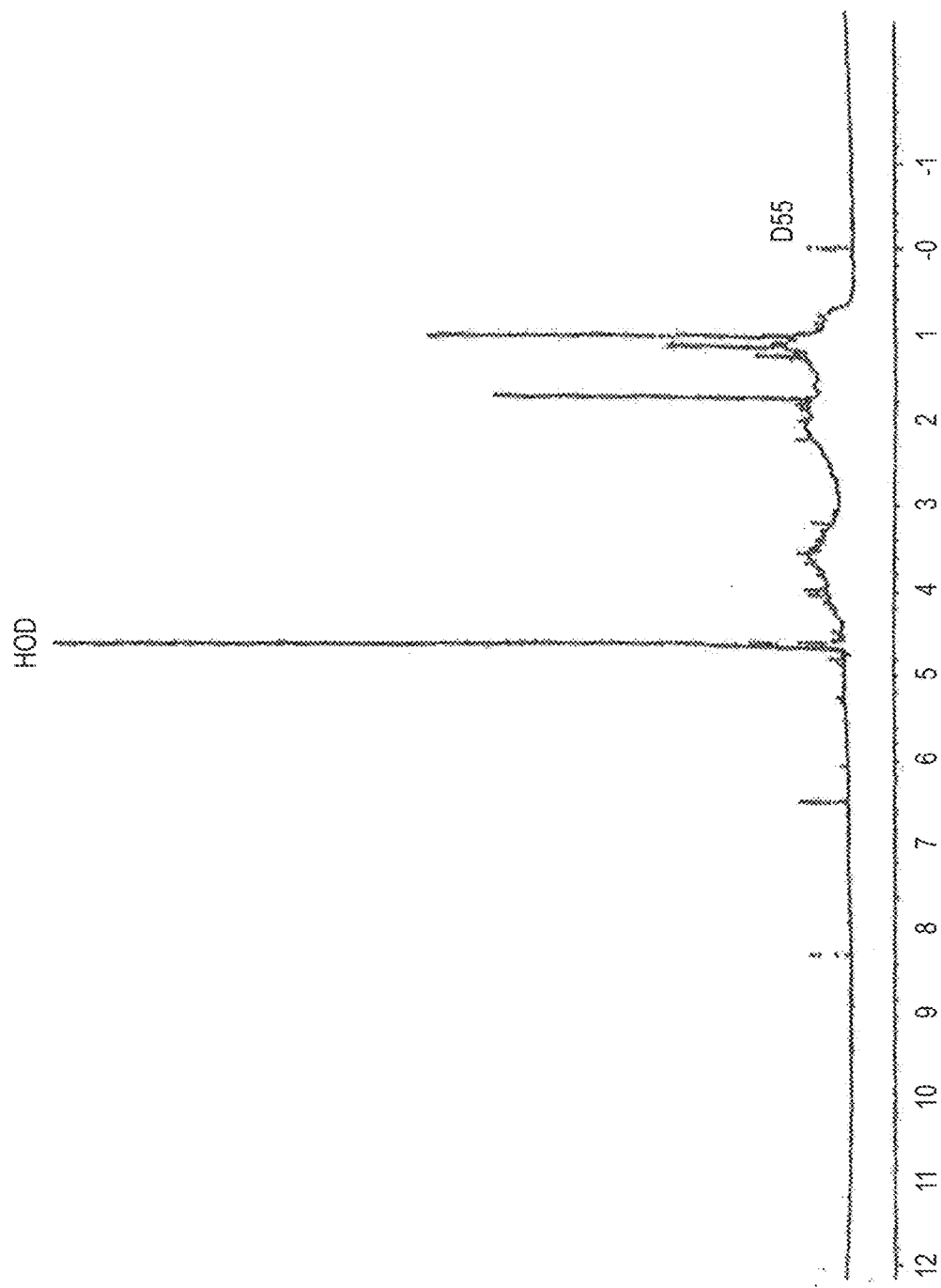

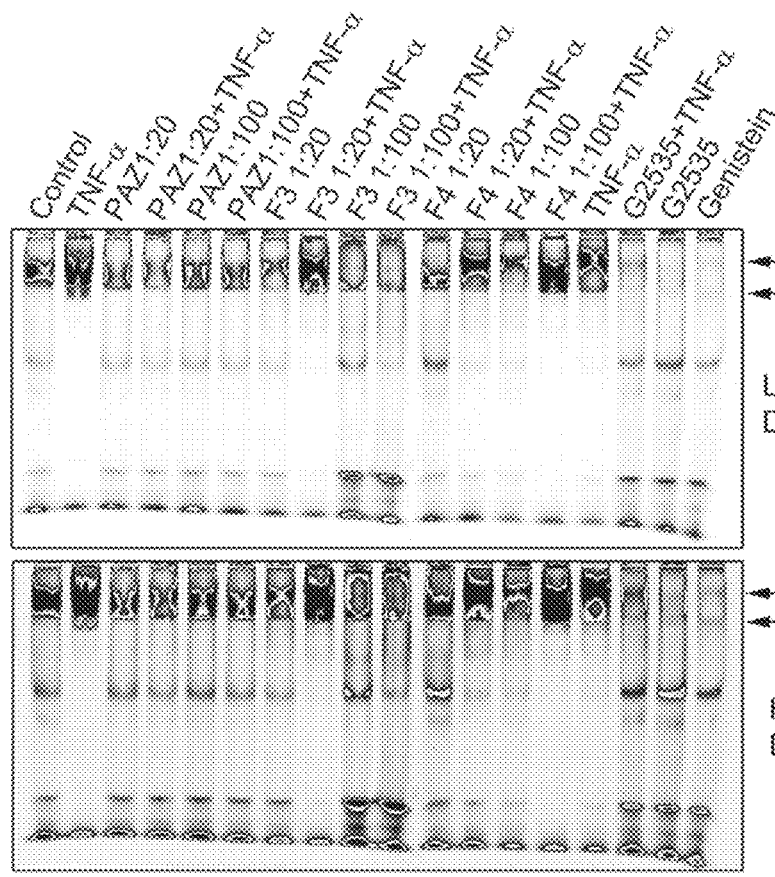

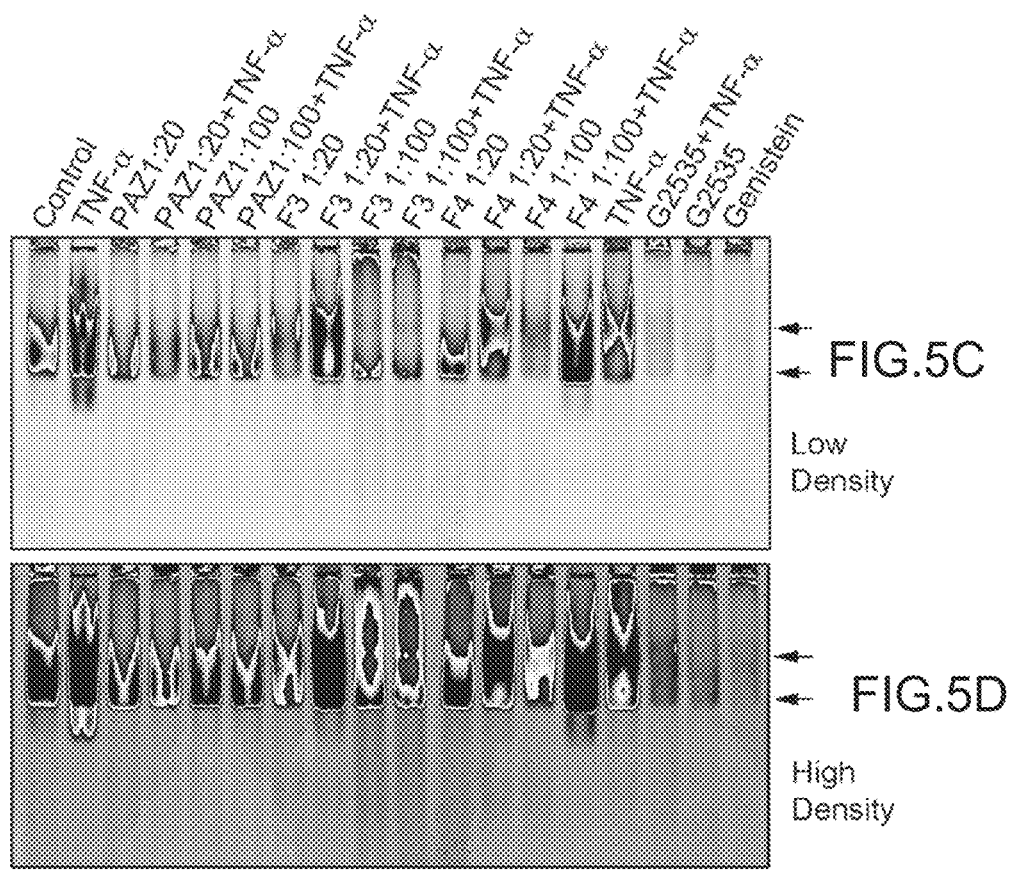

COMPOSITION AND METHOD FOR AFFECTING CYTOKINES AND NF-κB

CROSS-REFERENCE TO RELATED APPLICATIONS

This patent application is a continuation-in-part of and claims priority to U.S. patent application Ser. No. 13/841,739 filed on Mar. 15, 2013 entitled "Composition and Method for Affecting Cytokines and NF-κB" which is a continuation-in-part of U.S. patent application Ser. No. 12/897,574 (issued as U.S. Pat. No. 8,791,060) filed on Oct. 4, 2010 entitled "Composition and Use of Phyto-Percolate For Treatment of Disease" which is a continuation application of and claims priority to U.S. patent application Ser. No. 11/606,676 (issued as U.S. Pat. No. 7,807,622) filed on Nov. 30, 2006 entitled "Composition and Use of Phyto-Percolate for Treatment of Disease," which claims the benefit of priority to U.S. Provisional Application No. 60/741,774 filed on Dec. 7, 2005. The '676 application is also a continuation-in-part of International Application No. PCT/US06/15302 filed on Apr. 20, 2006 entitled "Composition and Use of Phyto-Percolate for Treatment of Disease," which claims the benefit of U.S. Provisional Application No. 60/741,774 filed Dec. 2, 2005 and 61/719,025 filed on Sep. 21, 2005. The '676 is also a continuation-in-part of International Application No. PCT/US05/13375 entitled "Method and Preparation of Use of Fibrinolytic Enzymes in the Treatment of Disease," which claims the benefit of U.S. Provisional Patent Application Ser. No. 60/565,011, filed on Apr. 23, 2004. The '739 patent application is also a continuation-in-part of U.S. patent application Ser. No. 12/947,684 filed on Nov. 16, 2010 and entitled "Composition and Method for Affecting Cytokines and NF-κB" which claims priority to and the benefit of U.S. Provisional Patent Application No. 61/261,639 filed Nov. 16, 2009, entitled "Composition and Method for Affecting Cytokines and NF-κB," wherein such provisional application is hereby incorporated in its entirety. The contents of all of these related applications are incorporated herein by reference in their entirety.

FIELD OF INVENTION

This invention generally relates to a composition and method for altering the production and/or function of proteins such as cytokines and transcription factors. More specifically, the present invention relates to a composition derived from the culture or co-culture of specific freshwater microorganisms, algae, moss, bacteria and/or fungi and a method of treating or preventing inflammation and/or diseases such as cancer and HIV by administering an effective amount of the composition.

BACKGROUND OF THE INVENTION

Cytokines are a broad class of proteins that are secreted by various cell types, including cells of the immune system. One function of cytokines is to carry various signals between cells and thus control activity among cells. Several factors can cause cells to secrete cytokines, including a cell's encounter with pathogens, which may cause disease. In certain instances, cells will secrete cytokines as a means of organizing a natural defense against the pathogen or disease.

There are numerous cytokines, many of which are commonly called interleukins ("IL") produced by white blood cells. In turn, there are numerous different interleukins such as, for example, IL-2, IL-10, and IL-17A. Each of these different interleukins has specific functions and effects such as decreasing or increasing inflammation, stimulating the proliferation and function of various cell types and regulating the production of antibodies. For example, IL-2 and TNF-α contribute towards inflammation and may be considered as inflammatory proteins while IL-10 may be considered an anti-inflammatory protein that decreases inflammation. Therefore, the more IL-2 and TNF-α produced, the greater the inflammation. Conversely, the more IL-10 produced the less inflammation.

Interleukins have been determined to be involved in many processes, including, but not limited to, inflammation. For example, there is substantial evidence suggesting that IL-2 suppresses the production of immunoglobulins. In contrast, there is substantial evidence suggesting that IL-10 enhances immunoglobulin production.

Another cytokine is interferon-gamma or IFN-γ. IFN-γ is critical for innate and adaptive immunity against viral and intracellular bacterial defense functions and for tumor control. IFN-γ has been shown to alter the transcription of over thirty genes and to produce such affects as increasing Th2 cell activity, promoting NK cell activity, and affecting various other molecular signaling pathways.

Other cytokines include tumor necrosis factor alpha or TNF-α which is involved in the regulation of immune cells. Further, elevated production of TNF-α has been implicated as a contributing factor in a variety of human diseases, including cancer. Yet another cytokine is granulocyte-macrophage colony-stimulating factor or GM-CSF. GM-CSF is a white blood cell growth factor that is known to stimulate stem cells, and is part of the immune/inflammatory cascade.

A transcription factor known as "nuclear factor kappa beta" or NF-κB is an intracellular protein that functions as a regulator of gene transcription and plays an important role in various biological processes and pathology. NF-κB has been found to play an important role in regulating the immune system in response to infection and in several inflammatory pathways including the production of cyclooxygenase, nitric oxide synthase and other pro-inflammatory proteins. Inappropriate regulation of NF-κB has been linked to cancer, inflammatory and autoimmune diseases, septic shock, viral infection, and improper immune development and certain studies have linked NF-κB to processes involving synaptic plasticity and memory. The role of NF-κB and various cytokines is discussed in the article entitled *Using Chemopreventive Agents to Enhance the Efficacy of Cancer Therapy* by Sarkar, et al. and published by the American Association for Cancer Research on Apr. 1, 2006 which is herein incorporate by reference in its entirety. Further, various viruses, including the HIV virus have molecular binding sites for NF-κB thus indicating the NF-κB may be a critical component for activating the HIV virus from a latent state to an active state.

Therefore, the regulation of cytokines and/or NF-κB can be a critical process in providing treatment for various ailments. For example, since IL-10 has anti-inflammatory properties, increasing IL-10 in a patient suffering from a chronic inflammatory condition can be used to treat the inflammation. Alternatively, since NF-κB is a factor for activating the HIV virus from a latent state to an active state, reducing the amount of NF-κB could delay or prevent the HIV virus from being activated.

Currently, there are known compositions and methods for regulating cytokines and NF-κB. However, many of these known compositions and methods are irritating to cells or have a toxic effect on cells. Further, many known compositions and methods for regulating cytokines and NF-κB regulate many cytokines in the same manner, some of which may hinder the overall desired effect of the treatment. For example, there are known compositions and methods for treating inflammation that up-regulate anti-inflammatory cytokines such as IL-10, but these compositions also result in the up-regulation of IL-2, an inflammatory cytokine that reduces the effect of the IL-10.

Therefore, it would be advantageous to provide an improved composition and method of regulating anti-inflammatory cytokines and NF-κB and effected these on a cellular level. Moreover, providing a composition and method that could regulate selected cytokines and NF-κB to achieve a multitude of effects to treat various health problems would be desirable. One example of such specific regulation of multiple cytokines would be a composition that up-regulates IL-10 without up-regulating IL-2, or even while downregulating IL-2, thus increasing anti-inflammatory cytokines while reducing or maintaining the level of pro-inflammatory cytokines in order to reduce inflammation. It would also be desirable to provide a composition and method to affect various cytokines and NF-κB that is not an irritant, is non-toxic, is easy to manufacture and distribute, and is not expensive to produce.

SUMMARY OF THE INVENTION

In one aspect, the invention provides a method for treating or preventing a disorder in a mammal (e.g., human, dog, cat, horse, etc.) by administering to the mammal a therapeutically effective amount of phyto-percolate or derivative thereof.

In useful embodiments, the phyto-percolate derivative is a protein having a molecular weight of about 67.5 kDa, a protein having a molecular weight of about 21.0 kDa, or a polysaccharide. In another embodiment, the phyto-percolate derivative has fibrinolytic enzymatic activity. The phyto-percolate derivative may be isolated from the phyto-percolate or it may be produced by any appropriate method known in the art. Suitable methods for producing the phyto-percolate derivative include, for example, recombinantly expressing the derivative (e.g., protein) by a microorganism and synthetically producing a derivative (i.e., chemical (cell-free) synthesis). The recombinant microorganism may be one or more of the species present in ATCC Deposit #PTA-5863, or it may be any other appropriate specie.

In particular embodiments a particular dosage is between about 1 and about 8 ounces per day of the phyto-percolate. Particularly noted is a dosage of about 1 to about 4 ounces per day. Preferably, the phyto-percolate that is administered to the human contains between about 10 ppm and about 150 ppm of a phyto-percolate derivative. In another useful embodiment, a therapeutically effective amount of one or more of the derivatives is administered to the human. Preferably, the mammal is administered between about 1 mg and 1000 mg of the derivative per day. Suitable methods for administration of the phyto-percolate include oral administration. Suitable methods for administration of a phyto-percolate derivative (e.g., an isolated derivative) include, for example, oral, topical, rectal, or vaginal administration as well as intravenous, intramuscular, and subcutaneous injection.

Another aspect of this invention is directed to a method of treating an overweight condition or obesity comprising administering to the mammal (e.g., human) a therapeutically effective amount of a phyto-percolate or derivative thereof.

Another aspect of this invention is directed to a method for treating type I and II diabetes comprising administering to the mammal (e.g., human) a therapeutically effective amount of a phyto-percolate or derivative thereof.

Another aspect of this invention is directed to a method for treating an inflammatory disorder comprising administering to the mammal (e.g., human) a therapeutically effective amount of a phyto-percolate or derivative thereof. It is believed that the phyto-percolate and derivatives have broad spectrum anti-inflammatory properties and therefore may be used to reduce or prevent inflammation in a wide range of diseases and disorders.

Another aspect of this invention is directed to a method for treating a stomach disorder comprising administering to the mammal (e.g., human) a therapeutically effective amount of a phyto-percolate or derivative thereof. Stomach disorders amenable to treatment with the phyto-percolate and/or derivatives thereof include, for example, a stomach ulcer and gastric reflux disease.

In another aspect of this invention, the phyto-percolate or derivatives may be used to alleviate side-effects of another primary therapy. For example, the phyto-percolate may be administered to reduce the oxidative stress, chemotherapy-induced nausea, chemotherapy-induced liver damage, appetite suppression, hair loss, fingernail and toenail loss and discoloration that result from anti-AIDS therapy and anti-cancer therapy (e.g., chemotherapy and radiation therapy).

In another aspect of this invention, the phyto-percolate or derivatives may be used to reduce the recovery time in mammals (e.g., humans and horses) after periods of stress (e.g., exercise). In a related aspect, the phyto-percolate or derivatives are administered in order to restore physical energy and mental acuity following periods of stress.

In another aspect of this invention, the phyto-percolate or derivates may also be administered topically directly to the eye (e.g., in the form of eye drops) to treat lesions of the cornea, dry eyes, and similar ocular disorders.

Another aspect of this invention is directed to a method for treating conditions or disorders associated with infectious disease (e.g., a viral infection) comprising administering to the mammal (e.g., human) a therapeutically effective amount of a phytopercolate or derivative thereof. Infectious disease may be the cause of many of the above and below listed diseases such as pneumonia, all viruses, acariosis, acne, adenovirus, AIDS, amebiasis, anthrax, athlete's food, babesiosis, bartonellosis, Bell's palsy, botulism, candidiasis, carbuncles, Chaga's disease, chicken pox, Chlamydia, coccidiomycosis, coronavirus, cryptococcosis, cytomegalovirus, Dengue fever, echovirus, erysipelas, furuncle, gangrene, Guillan-Barre syndrome, hepatitis, impetigo, influenza, leucopenia, Lyme's disease, malaria, martolditis, measles, mumps, *mycobacterium*, mycosis, parasites, pediculosis, P.I.D. pyodermia, rabies, rubella, *salmonella*, salpingitis, septicemia, shingles, sinusitis, syphilis, tetanus, Tindi Cruzi and warts.

Another aspect of this invention is directed to a method for treating diseases related to the heart, blood vessels, renal, liver, and endocrine system comprising administering a therapeutically effective amount of a phyto-percolate or derivative thereof.

Another aspect of this invention is directed to a method for treating a vasospasm comprising administering to a mammal (e.g., human) a therapeutically effective amount of a phyto-percolate or derivative thereof.

Another aspect of this invention is directed to a method for treating heart failure comprising administering to a mammal (e.g., human) a therapeutically effective amount of a phyto-percolate or derivative thereof.

Another aspect of this invention is directed to a method for treating cardiac hypertrophy comprising administering to a mammal (e.g., human) a therapeutically effective amount of a phyto-percolate or derivative thereof.

Another aspect of this invention is directed to a method for treating dysregulated blood pressure comprising administering to a mammal (e.g., human) a therapeutically effective amount of a phyto-percolate or derivative thereof.

Another aspect of this invention is directed to a method for treating angina comprising administering to a mammal (e.g., human) a therapeutically effective amount of a phyto-percolate or derivative thereof.

Another aspect of this invention is directed to a method for treating peripheral vascular disease comprising administering to a mammal (e.g., human) a therapeutically effective amount of a phyto-percolate or derivative thereof.

Another aspect of this invention is directed to a method for treating cerebral diseases and diseases related to the central nervous system that are vascular in origin comprising administering to a mammal (e.g., human) a therapeutically effective amount of a phytopercolate or derivative thereof.

Another aspect of this invention is directed to a method for treating neurodegeneration comprising administering to a mammal (e.g., human) a therapeutically effective amount of a phyto-percolate or derivative thereof.

Another aspect of this invention is directed to a method for treating Alzheimer's disease comprising administering to a mammal (e.g., human) a therapeutically effective amount of a compound of a phyto-percolate or derivative thereof.

Another aspect of this invention is directed to a method for treating depression comprising administering to a mammal (e.g., human) a therapeutically effective amount of a phyto-percolate or derivative thereof.

Another aspect of this invention is directed to a method for treating addiction, including drug detoxification and/or substance abuse including nicotine, cocaine and alcohol abuse comprising administering to a mammal (e.g., human) a therapeutically effective amount of a phyto-percolate or derivative thereof.

Another aspect of this invention is directed to a method for treating attention deficit disorder and attention deficit hyperactivity disorder comprising administering to a mammal (e.g., human) a therapeutically effective amount of a compound of a phyto-percolate or derivative thereof.

Another aspect of this invention is directed to a method for treating sleep disorders comprising administering to a mammal (e.g., human) a therapeutically effective amount of a phyto-percolate or derivative thereof.

Another aspect of this invention is directed to a method for treating seasonal affective disorder comprising administering to a mammal (e.g., human) a therapeutically effective amount of a phyto-percolate or derivative thereof.

Another aspect of this invention is directed to a method for treating environmental and food allergies comprising administering to a mammal (e.g., human) a therapeutically effective amount of a phyto-percolate or derivative thereof.

Another aspect of this invention is directed to a method for treating conditions related to pain or nocioception comprising administering to a mammal (e.g., human) a therapeutically effective amount of a phyto-percolate or derivative thereof.

Another aspect of this invention is directed to a method for treating migraine comprising administering to a mammal (e.g., human) a therapeutically effective amount of a compound of a phyto-percolate or derivative thereof.

Another aspect of this invention is directed to a method for treating disorders related to disruption of circadian rhythms including jet lag comprising administering to a mammal (e.g., human) a therapeutically effective amount of a phyto-percolate or derivative thereof.

Another aspect of this invention is directed to a method for treating diseases related to abnormal gastrointestinal motility, secretion, and/or function comprising administering to a mammal (e.g., human) a therapeutically effective amount of a phyto-percolate or derivative thereof.

Another aspect of this invention is directed to a method for treating diarrhea and/or incontinence comprising administering to a mammal (e.g., human) a therapeutically effective amount of a phyto-percolate or derivative thereof.

Another aspect of this invention is directed to a method for treating a gastric ulcer comprising administering to a mammal (e.g., human) a therapeutically effective amount of a phyto-percolate or derivative thereof.

Another aspect of this invention is directed to a method for treating irritable bowel syndrome comprising administering to a mammal (e.g., human) a therapeutically effective amount of a phyto-percolate or derivative thereof.

Another aspect of this invention is directed to a method for treating inflammatory bowel disease comprising administering to a mammal (e.g., human) a therapeutically effective amount of a phyto-percolate or derivative thereof.

Another aspect of this invention is directed to a method for treating nausea comprising administering to a mammal (e.g., human) a therapeutically effective amount of a phyto-percolate or derivative thereof.

Another aspect of this invention is directed to a method for treating sexual dysfunction comprising administering to a mammal (e.g., human) a therapeutically effective amount of a phyto-percolate or derivative thereof.

Another aspect of this invention is directed to a method for altering fertility comprising administering to a mammal (e.g., human) a therapeutically effective amount of a phyto-percolate or derivative thereof.

Another aspect of this invention is directed to a method for treating conditions or disorders associated with the immune system comprising administering to a mammal (e.g., human) a therapeutically effective amount of a phyto-percolate. Immune system deficiency may be the cause of many of the above and below listed diseases such as cancer, emphysema, encephalitis, environmental sensitivity, erysipelas, food poisoning and Reynaud's disease.

Another aspect of this invention is directed to a method for treating conditions or disorders associated with hormonal imbalances comprising administering to a mammal (e.g., human) a therapeutically effective amount of a phyto-percolate. Hormonal imbalances may be the cause of many of the above and below listed diseases such as acne, Addison's disease, endometriosis, Grave's disease, osteoporosis, menstrual and menopausal regulation, glucose, and other metabolic regulation. In this regards, the phyto-percolate and derivatives may be used to improve the general health and overall function of metabolic organs like the kidney, liver, and pancreas. It is believed that the phyto-percolate and derivatives improve the efficiency of those organs and increases their metabolic and endocrine functions.

Another aspect of this invention is directed to a method for treating conditions or disorders associated with neurological deficiencies comprising administering to a mammal (e.g., human) a therapeutically effective amount of a phyto-percolate. Neurological deficiencies may be the cause of many of the above and below listed diseases such as Lou Gehrig's disease, chronic pain, Huntingdon's Chorea, diabetic neuropathy, multiple sclerosis, Myasthenia Gravis, Parkinson's disease, poliomyelitis, senile dementia, nigrostriatal degeneration, stroke, tardive dyskinesia and tinnitus.

Another aspect of this invention is directed to a method for treating respiratory diseases comprising administering to a mammal (e.g., human) a therapeutically effective amount of a phyto-percolate.

Another aspect of this invention is directed to a method for treating asthma comprising administering to a mammal (e.g., human) a therapeutically effective amount of a phyto-percolate.

Another aspect of this invention is directed to a method for treating diseases related to abnormal hormone release and utilization comprising administering to a mammal (e.g., human) a therapeutically effective amount of a phyto-percolate.

Another aspect of this invention is directed to a method for treating abnormal insulin release and utilization comprising administering to a mammal (e.g., human) a therapeutically effective amount of a compound of a phyto-percolate.

Another aspect of this invention is directed to a method for treating skin lesions and disorders.

In addition to the "direct" effect of the phyto-percolate of this invention there are diseases/conditions wherein subjects with said diseases/conditions will benefit from the associated weight loss, and metabolic and immune system regulation, such as insulin resistance with impaired glucose tolerance, Type II Diabetes, hypertension, hyperlipidemia, cardiovascular disease, gall stones, certain cancers, sleep apnea, etc. resulting from use of phyto-percolate.

In a further illustrative embodiment a method of making the inventive phytopercolate is disclosed. The phyto-percolate is prepared by cultivating a mixture of freshwater algae and bacteria that is augmented by a nutrient blend that is related to the production of fibrinolytic enzymes, proteins, and other molecules, forming a fortified algae culture. Added to this fortified algal and bacterial culture is purified fresh water that has been purified by reverse osmosis, distillation and/or deionization. The culture is percolated with said purified fresh water and nutrient blend for a predetermined time forming a phytopercolate that is fibrinolytic and proteinaceous in nature. The phyto-percolate is decanted from the fortified algal and bacterial culture and processed. Suitable methods of processing the phyto-percolate include filtration, centrifugation, lyophilization, purification, dilution, and other methods. The filtering of the decanted phyto-percolate in one particular embodiment is by micro-filtration where the micro-filtration removes particles larger than about 0.22 µm.

In another aspect, this invention provides a substantially pure compound isolated from a phyto-percolate. In a preferred embodiment, the compound is isolated from the percolate produced by culturing the microorganisms of ATCC Deposit #PTA-5863 or other appropriate species as described herein. In another embodiment, the compound is a protein having a molecular weight of about 67.5 kDa.

In a related aspect, the invention provides a pharmaceutical formulation comprising a substantially pure compound isolated from a phyto-percolate and a pharmaceutically acceptable excipient.

The term "inflammatory disorder" encompasses a variety of conditions including conditions related to a hyperactive immune system, chronic inflammation, and autoimmune disorders. Inflammatory disorders include, for example, acne vulgaris; acute febrile neutrophilic dermatosis; acute respiratory distress syndrome; Addison's disease; adrenocortical insufficiency; adrenogenital ayndrome; allergic conjunctivitis; allergic rhinitis; allergic intraocular inflammatory diseases, ANCA-associated small-vessel vasculitis; angioedema; ankylosing spondylitis; aphthous stomatitis; arthritis, asthma; atherosclerosis; atopic dermatitis; autoimmune disease; autoimmune hemolytic anemia; autoimmune hepatitis; Behcet's disease; Bell's palsy; berylliosis; balanitis circumscripta plasmacellularis; balanoposthitis; bronchial asthma; bullous herpetiformis dermatitis; bullous pemphigoid; carditis; celiac disease; cerebral ischaemia; chronic obstructive pulmonary disease; cirrhosis; Cogan's syndrome; contact dermatitis; COPD; Crohn's disease; Cushing's syndrome; dermatomyositis; diabetes mellitus; discoid lupus erythematosus; eczema (e.g., asteatotic eczema, dyshidrotic eczema, vesicular palmoplantar eczema); eosinophilic fasciitis; epicondylitis; erythema annulare centrifugum; erythema dyschromicum perstans; erythema multiforme; erythema nodosum; exfoliative dermatitis; fibromyalgia; focal glomerulosclerosis; giant cell arteritis; gout; gouty arthritis; graftversus-host disease; granuloma annulare; hand eczema; Henoch-Schonlein purpura; herpes gestationis; hirsutism; hypersensitivity drug reactions; idiopathic cerato-scleritis; idiopathic pulmonary fibrosis; idiopathic thrombocytopenic purpura; inflamed prostate; inflammatory bowel or gastrointestinal disorders, inflammatory dermatoses; juvenile rheumatoid arthritis; laryngeal edema; lichen nitidus; lichen planus; lichen sclerosus et atrophicus; lichen simplex chronicus; lichen spinulosus; Loeffler's syndrome; lupus nephritis; lupus vulgaris; lymphomatous tracheobronchitis; macular edema; multiple sclerosis; muscu-loskeletal and connective tissue disorder; myasthenia gravis; myositis; nummular dermatitis; obstructive pulmonary disease; ocular inflammation; organ transplant rejection; osteoarthritis; pancreatitis; pemphigoid gestationis; pemphigus vulgaris; polyarteritis nodosa; polymyalgia rheumatica; primary adrenocortical insufficiency; primary billiary cirrhosis; pruritus scroti; pruritis/inflammation, psoriasis; psoriatic arthritis; Reiter's disease; relapsing polychondritis; pyoderma gangrenosum; rheumatic carditis; rheumatic fever; rheumatoid arthritis; rosacea caused by sarcoidosis; rosacea caused by scleroderma; rosacea caused by Sweet's syndrome; rosacea caused by systemic lupus erythematosus; rosacea caused by urticaria; rosacea caused by zoster-associated pain; sarcoidosis; scleroderma; segmental glomerulosclerosis; septic shock syndrome; serum sickness; shoulder tendinitis or bursitis; Sjogren's syndrome; Still's disease; stroke-induced brain cell death; Sweet's disease; systemic dermatomyositis; systemic lupus erythematosus; systemic sclerosis; Takayasu's arteritis; temporal arteritis; thyroiditis; toxic epidermal necrolysis; tuberculosis; type-1 diabetes; ulcerative colitis; uveitis; vasculitis; and Wegener's granulomatosis.

The term "substantially pure," when referring to a protein or other derivative of the phyto-percolate, means the state of a substance that has been separated from the other components of the phyto-percolate. Typically, a substantially pure derivative is at least 80%, by weight, free from the other proteins and other molecules of the phyto-percolate. Preferably, the substantially pure derivative is at least 90%, 95%, or 99%, by weight, free from those organic molecules. A substantially pure protein derivative may be obtained, for example, by extracting it from a source other than the phyto-percolate. A protein derivative, for example, may be recombinantly expressed in another microorganism or in a cell-free translation system.

In accordance with yet another aspect of the present invention and as set forth in the detailed description and in accordance with various embodiments of the present invention, a composition and method for effecting cytokines and NF-κB is disclosed. According to one exemplary embodiment, the composition is derived from the culture or co-culture of specific freshwater microorganisms, algae, moss, bacteria and/or fungi of ATCC Deposit No. PTA-5863.

According to various exemplary embodiments of the present invention, a method of effecting cytokines and NF-κB to regulate immune response, reduce inflammation, provide antioxidant activity, modulate antibody production, treat or prevent cancerous tumor growth, and treat or prevent infections including HIV is disclosed. The composition is non-toxic and is capable of selectively up-regulating certain cytokines such as IL-10 while maintaining or reducing other cytokines such as IL-2 and/or TNF-α to achieve a desired result, such as reduced inflammation. In still yet other exemplary embodiments of the present invention, a method of affecting the DNA-binding activity of NF-κB and a method of reducing TNF-α-induced activation of NF-κB is disclosed. Further, according to various exemplary embodiments of the present invention, methods of inducing certain anti-inflammatory cytokines such as IL-10, particularly while not inducing other pro-inflammatory cytokines such as IL-2, TNF-α and IFN-γ is disclosed.

BRIEF DESCRIPTION OF THE DRAWINGS

The foregoing and other features and advantages of the present invention will be more fully understood from the following detailed description of illustrative embodiments, taken in conjunction with the accompanying drawing in which:

FIG. 4 is a [$^1$H]-NMR spectrum of the diluted phyto-percolate;

FIGS. 5A-5D illustrate raw data from electrophoretic gel mobility shift assays according to various exemplary embodiments of the present invention;

DETAILED DESCRIPTION

Figure 1:
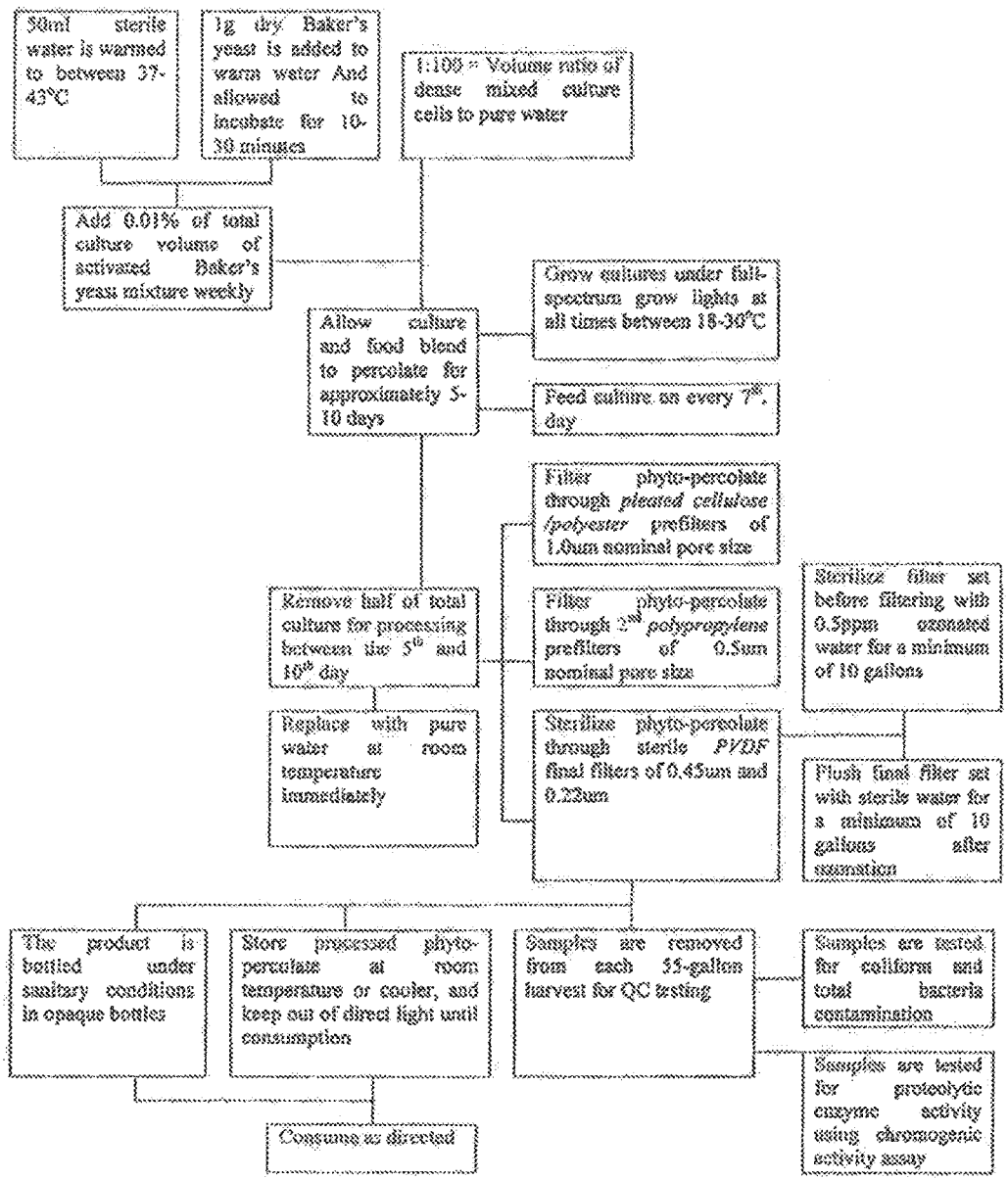
FIG. 1 is a flow chart showing a method of preparing a phyto-percolate.

The present invention provides a phyto-percolate that has therapeutic and other beneficial properties when administered to humans and other animals. Without being bound by any theory, it is believed that at least one of the therapeutically active agents in the phyto-percolate is an enzyme. Methods for preparing the phyto-percolate are also provided. Detailed embodiments of the present invention are disclosed herein, however, it is to be understood that the disclosed embodiments are merely exemplary of the invention, which may be embodied in various forms. Therefore, specific functional details disclosed herein are not to be interpreted as limiting, but merely as a basis for the claims and as a representative basis for teaching one skilled in the art to variously employ the present invention in virtually any appropriately detailed embodiment.

Phyto-Percolate Production

According to the invention, a phyto-percolate is derived from a culture comprised of freshwater algae, moss, bacteria, actinomycetes, and fungi. It is believed that the culture is comprised of at least one or more of the following genera:

*Acinetobacter*
*Aerococcus*
*Aquaspirillium*
*Bacillus*
*Brevibacterium*
*Caseobacter*
*Chlorella*
*Clavibacter*
*Corynebacterium*
*Dermacoccus*
*Liefsonia*
*Micrococcus*
*Oedocladium*
*Phyllobacterium*
*Pseudomonas*
*Ralstonia*
*Rhizobium*
*Rhodococcus*
*Riemerella*
*Shingomonas*
*Staphylococcus*
*Stenotrophomonas*
*Stichococcus*
*Streptomyces*
*Ulothrix*
*Variovorax*
*Weeksella*
*Xanthomonas*

Particular note is made of the genera *Aquaspirillum, Bacillus, Pseudomonas, Ralstonia, Stenotrophomonas, Stichococcus,* and *Ulothrx*. Without being bound by any theory, it is believed that these genera are the most abundant organism in each culture and may be the primary producers of the phyto-percolate derivatives. A deposit of a culture resulting in a phyto-percolate of the present invention was deposited on Mar. 17, 2004 in the American Type Culture Collection, of Manassas, Va., as Deposit #: PTA-5863, having the description "unicellular green algae species, filamentous green algae species, rotifer species, and gram negative bacteria." This deposit is available to the public upon grant of a patent disclosing the same. This deposit was made pursuant to 37 C.F.R. § 1.808 and MPEP § 2410.01 and therefore, access to the deposit will be available during pendency of this application making reference to the deposit to one determined by the Commissioner to be entitled thereto under 37 C.F.R. § 1.14 and 35 U.S.C. § 122 and with one exception, that all restrictions imposed by the depositor on the availability to the public of the deposited biological material be irrevocably removed upon the granting of the patent.

In particular embodiments, a heterotrophic rotifer species exists in the cultures, as well as bacteria that have been identified as *Stenotrophomonas maltophilia, Ralstonia pickettii, Ralstonia paucula, Acinetobacter genospecies* 11, *Acinetobacter junii, Leifsonia aquatica, Riemerella anatipestifer, Variovorax paradoxes*, and *Streptomyces griseorubens*. Without being bound to any particular theory, it is believed that these species may produce compounds that are contributors to the effectiveness of the phyto-percolate.

A method of producing phyto-percolate is depicted in FIG. 1. Phyto-percolate cultures of approximately 100-200 ml of dense algal cells in approximately 2.5 gal, or approximately 10 liters, of reverse-osmosis purified sterile water are fed about 1 milliliter (ml) per week of liquid extract of live active yeast, or Baker's yeast, *Saccharomyces cerevisiae*, which has been prepared from 1.0 g dry active yeast added to 50 ml warm water, at between about 37° and about 43° C. The mixture is allowed to incubate for 10-30 minutes, or until it slightly foams. The cultures are fed in either 1.0 ml weekly doses, or 0.5 ml twice-weekly doses. It is contemplated within the scope of the invention that other yeast cultures may be used. It is further contemplated that other organic nutrients or substrates known in the art may be used such as glucose or proteose, or other algal growth media prepared from inorganic nutrients, supplements, and/or vitamins.

In one embodiment, the cultures are grown under full-spectrum grow lights at about 25° C., and produce a final unadjusted pH of between about 6.2 to about 7 that fluctuates. The cultures are grown in clear glass fishbowl containers having a volume of approximately 2.5 gal with semi-transparent plastic lids, with the exception of about a 3 mm hole in the lid for gas exchange. It is contemplated within the scope of the invention that other culture containers, ingredients, conditions and methods known in the art may be used that allow the cells to grow in a manner in which the phyto-percolate derivatives are expressed. Such methods may include larger batch, semi-continuous, continuous or other type culture systems including bireactors or photore-actors, may or may not include aeration or agitation, may or may not include solid, liquid, semi-solid or other form of growth media or substrate, may or may not include the above particular conditions of temperature, contact time or area, or light intensity.

In this particular embodiment the cultures are harvested weekly or bi-weekly, between the 5th and 10th day after feeding, by drawing off the top 1.25 gal of phytopercolate from each 2.5 gal culture. This is referred to as the "raw phyto-percolate." The algal or other cells and yeast food forming the phyto-percolate culture remain in the bottom of the culture container substantially undisturbed while the phyto-percolate is decanted. The decanted material is then processed as desired. The volume of the container is then optionally returned to original volume. Conveniently this is accomplished with reverse osmosis purified water at approximately room temperature, about 25° C. It is contemplated within the scope of the invention that other culture and harvest systems, timetables volumes and methods may be used that result in phyto-percolate derivatives.

Without being bound by any particular theory, it is believed the patterns of harvest and feeding affect enzyme production. It is believed that more frequent smaller feedings such as 0.5 ml twice-weekly may stimulate greater enzyme production than single large amount feedings such as 2 ml bi-weekly, while discouraging contamination with undesirable bacteria and rotifer colonization. Since enzyme systems are highly dynamic and are directly affected by the immediate surroundings, the suggestion is supported that a food blend such as a liquid extract of active Baker's yeast increases the active proteolytic enzymes in the phyto-percolate culture compared with other foods or nutrient blends.

The peaks of enzyme concentration in the percolate over the course of several weeks are mapped under various feeding regimens, and serve to dictate the optimal date for harvests. According to the invention, the enzyme concentration is analyzed in the cultures and processed phyto-percolate to detect any negative effects of regular harvesting on the algal cultures over time, and is combined with data on the effects of environmental and stress factors such as dark/light, starvation, and/or changes in temperature or pH, which may stimulate or discourage enzyme production. Methods for analyzing these parameters include the isolation and homogenization of select cultures to eliminate all variables besides those being tested, and include monitoring of chlorophyll, total protein and enzyme activity, utilizing spectro-photometric methods, to measure the health and enzyme activity of the cultures over the course of an isolated-variable experiment.

In this particular embodiment the method for analyzing proteolytic activity is a typical chromogenic assay using Chromogenix substrate from DiaPharma, S-2251: chromogenic substrate for plasmin and streptokinase-activated plasminogen. Chromogenic substrates are peptides that react with proteolytic enzymes and proportionally change color as the substrate is lysed by the enzymes. The color change may be measured spectrophotometrically over time and is proportional to the proteolytic activity. The synthetic chromogenic assay substrates are designed to have enzyme binding selectivity similar to that of the enzyme's natural substrate. It is believed that the enzymes present in phyto percolate are selective for substrates including fractionated proteins and fibrin. It is contemplated within the scope of the invention that other methods for analyzing proteolytic activity and phyto-percolate derivatives may be used.

Enzyme activity for samples of described phyto-percolate currently ranges from 15-50 mU/mL of plasmin-like activity, when phyto-percolate is prepared as described. These values have been found to correlate with clinical observations of reduced pathological fibrin in humans orally consuming phyto-percolate. Methods for evaluating in vivo effects of phyto-percolate include peripheral blood observations on wet and dry blood smears, diagnostic and/or analytical blood tests, and various clinical observations and measurements such as body weight. Reductions in excess pathological fibrin and platelet aggregation have been observed, which are secondary to inflammation and tissue destruction. Changes in white blood cell mobility and number have also been observed. Anti-inflammatory effects of phyto-percolate in vivo have also been monitored with independent blood laboratory studies focusing on chronic inflammatory activity and hyper-coagulant states.

In an alternative embodiment, the phyto-percolate may be produced using a continuous culture format in which the phyto-percolate is substantially continuously removed from the culture and the lost volume is replaced with fresh culture media and/or nutrients. Further, the phyto-percolate may be produced using a bioreactor that is suitable for production on a larger scale than the batch culture method described above.

Phyto-Percolate Filtration

After harvest of the phyto-percolate from the cultures, the decanted fluid is filtered through a series of depth prefilters and sterile membrane filters made of low-protein binding materials. Examples of suitable final sterilizing filters are provided by Millipore Corp. Durapore brand filters, made of PVDF material. These have been shown to protect the enzyme concentration, and provide a final sterile filtration level of about 0.22 microns, as well as being chemically inert to ozonated water. Ozonated water is used for sterilizing the filter system, as it does not leave a damaging residue like chlorine.

All filters are 10" cartridge membrane or depth filters of various chemically-inert materials. The prefilters are housed in cartridge filter housings made of styrene-acrylonitrile (SAN). The final filters are housed in polypropylene (PP) housings with Kynar fittings. The material is harvested and filtered using Tygon tubing, peristaltic pumps and 55 gallon containers or other containers that have been pre-sterilized with ozonated water.

The phyto-percolate passes through a filtration regimen comprised of two pre-filters in SAN housings of pore size 1 μm (nominal), made of pleated cellulose/polyester. Examples of these filters are manufactured by Cole-Parmer, Vernon Hills, Ill., USA, catalog number EW-29830-20. It is contemplated within the scope of the invention that other filters know in the art may be used in this step as pre-filters, that are chemically inert.

The phyto-percolate is again filtered using a second stage pre-filter made of polypropylene in a polypropylene housing, with a nominal pore size of about 0.5 um. In one illustrative embodiment, this finishing filter is manufactured by Millipore Corporation, Bedford, Mass., Durapore® brand, Catalog #D00501S01. It is contemplated within the scope of the invention that other filters known in the art may be used in this step as second pre-filters, that are chemically inert.

The phyto-percolate is then passed through a pre-sterilized final filter that sterile-filters the phyto-percolate and removes all traces of bacteria, yeast, mold, algae and other particle contaminants. According to the invention, a final filter set consists of sterile membrane filters in PP housing having progressively smaller pore sizes of 0.45 um and 0.2211μ (absolute). These finishing filters' membranes are made of hydrophilic extremely-low protein-binding PVDF. In one illustrative embodiment, these finishing filters are manufactured by Millipore Corporation, Durapore® brand, Catalog #'s CVHIO1TPE and CVDIO1TPE. It is contemplated within the scope of the invention that other filters know in the art may be used that are inert to the phyto-percolate derivatives and processing and sanitizing materials including ozonated water. It is also contemplated within the scope of the invention that other methods of processing may be used.

Filtration by size exclusion removes approximately >99.9% of contaminants such as bacteria, yeast and mold spores, and algal cells. It is also believed to preserve enzymatic activity if filter materials are made of low-protein-binding, chemically-inert materials. The resulting liquid, the phyto-percolate, is substantially comprised of water, active enzymes, proteins and sugars. The phyto-percolate, after passing through the finishing filter is then usefully stored in sealed sterile 55 gal HDPE drums at between 21° and 27° C. until bottling. Samples are taken from each batch immediately after filtering to test for enzyme efficacy and contamination and for standardization. It is contemplated within the scope of the invention that other methods of sampling and testing may be used. The acceptable values for fibrinolytic enzyme efficacy to be administered p.o. are observed in the phyto-percolate as between 0 and 50 milli-units of plasmin-like activity; however higher levels may provide greater therapeutic benefit. It is believed that this filtered phyto-percolate contains approximately 50 ppm of the 67.5 kDa protein (see below).

The phyto-percolate is processed and bottled under sanitary conditions known in the art using ozone sterilization. It is believed that this step avoids enzyme degradation associated with the use of chlorine or heat sterilization because ozone leaves no residue if left to dissipate, or if followed by a rinse of sterile water. It is contemplated within the scope of the invention that other methods of filtration and sanitization known in the art may be used that are not unreasonably degrading of the enzymatic or other activity. The phytopercolate is usefully packaged in opaque UV-protectant bottles and shipped with cold packs to reduce product degradation. It is contemplated within the scope of the invention that other methods of packing, bottling, storing, and transporting may be used.

Phyto-Percolate Characterization

Raw phyto-percolate, prior to filtration, is a complex mixture of macromolecules. It is expected that the filtration process described above reduced the molecular complexity of the phyto-percolate filtrate. Several physico-chemical tests were performed to determine the composition of the filtrate. In each case, the phyto-percolate filtrate was lyophilized, redissolved in ddH20, and refiltered to remove any undissolved particulate matter.

Figure 2:
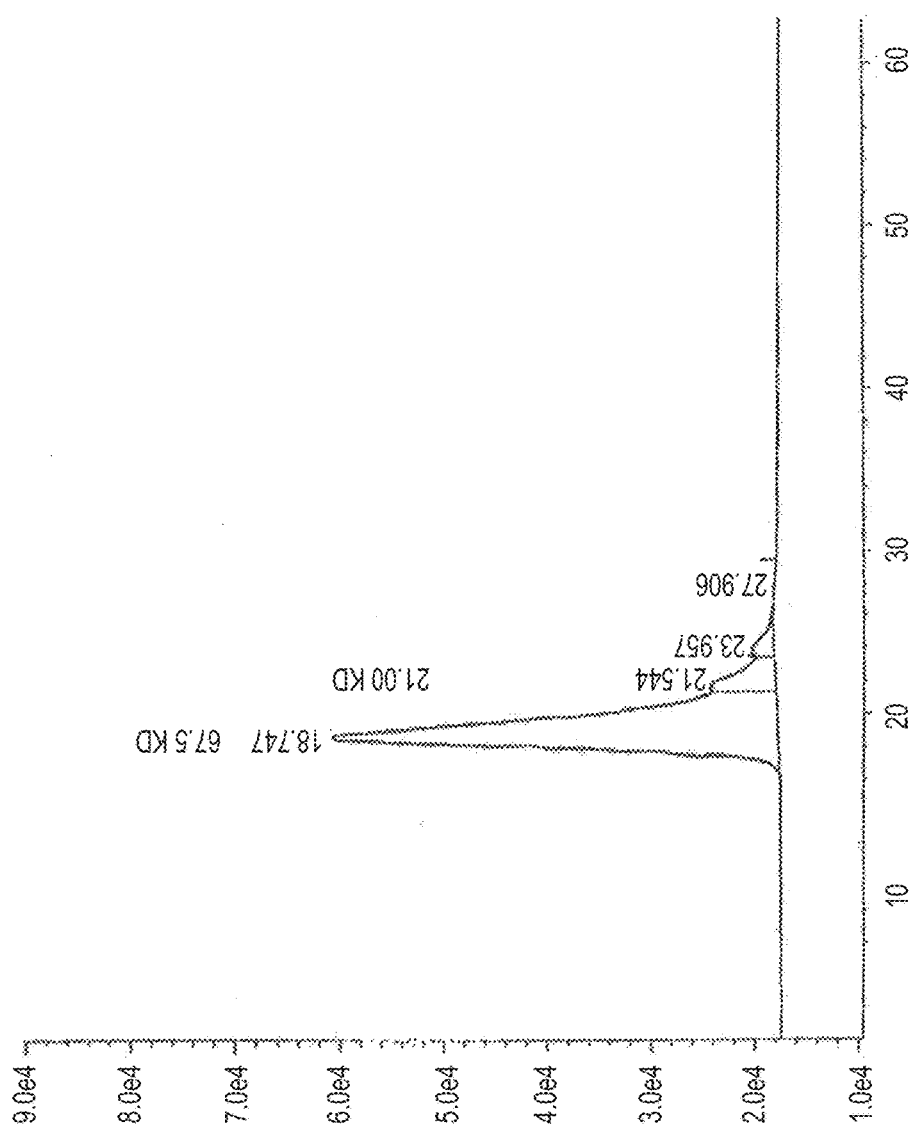
FIG. 2 is an FIPLC chromatogram of the diluted phyto-percolate.

A sample of the lyophilized phyto-percolate was subjected to isocratic reverse phase HPLC, on a size-exclusion chromatography column (TSK-GEL Super SW Series; Tosoh Biosciences, Montgomeryville, Pa.), under non-denaturing conditions. Proteins were identified using a micro flow cell UV detector at 280 nm. As shown in FIG. 2, a major protein species of 67.5 kDa was identified (retention time 18.747 minutes). The 67.5 kDa peak contributed about 90% of the total signal measured at 280 nm. Also detected were peaks at retention times of 21.544 minutes (21.0 kDa) and 23.957 minutes. Analysis under denaturing and other conditions indicates that the 21.0 kDa species is a protein molecule and the 23.957 minute peak is primarily polysaccharide. The major components of the phyto-percolate (the 67.5 kDa protein, 21.0 kDa protein, and the polysaccharide identified at 23.957 minutes) are referred to herein as phyto-percolate derivatives and may contribute to the biological and therapeutic efficacy of the phyto-percolate.

Figure 3:
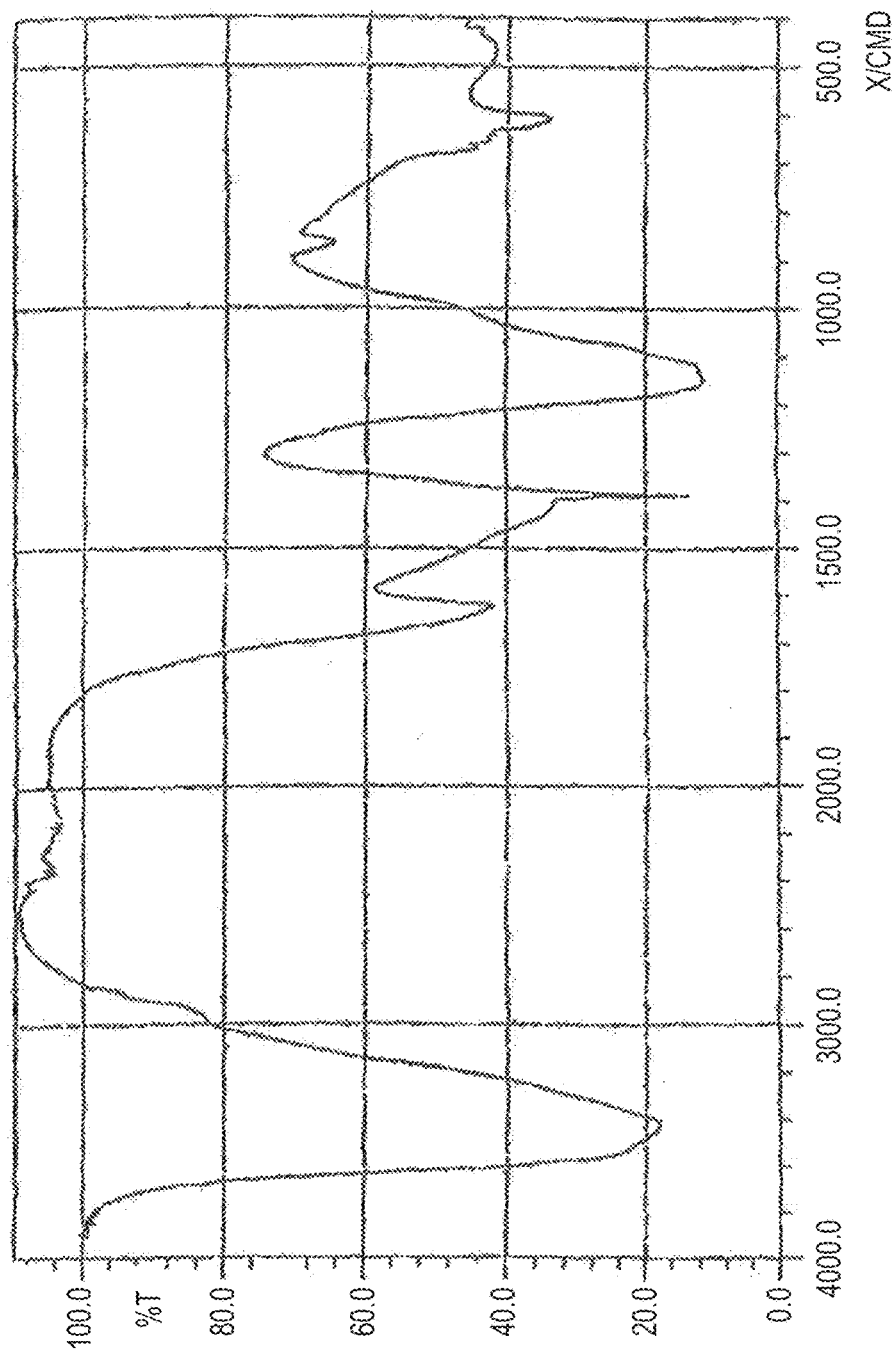
FIG. 3 is an FTIR spectrum of the diluted phyto-percolate.

Another sample of the lyophilized phyto-percolate was subjected to Fourier Transform Infrared (FTIR) spectroscopy. The results are provided in FIG. 3. FIG. 3 shows a spectrum that is characteristic of a dissolved protein sample.

A third sample of the lyophilized phyto-percolate was used for [1H]-NMR. The NMR spectrum is provided in FIG. 4. Here again, the results are consistent with a single protein species.

Weight Management Using Phyto-Percolate

Excessive weight has emerged as a prominent and growing health problem. Greater than 61% of Americans over the age of 20 are overweight, 25% of whom are obese. Second only to tobacco use as the top underlying preventable cause of death, excessive weight is a major risk factor for developing diabetes, heart disease, hypertension, gallbladder disease, arthritis, lung diseases, and certain types of cancer.

Example 1: Rodent Model of Weight Loss

A 21 day weight loss study using twelve mature (12 month old) Sprague-Dawley rats was performed. Each animal was orally administered 10 ml/kg of undiluted and unfiltered phyto-percolate (i.e., raw phyto-percolate) for 14 days, followed by non-dosing for 7 days. Each animal was weighted daily and observed for signs of toxicity. As shown in more detail in Table 1, the rats lost an average of 33 grams (6.3%) of body weight over the initial 14 day dosing period. They immediately began to regain lost body weight upon cessation of phyto-percolate administration. By the 21 day time point (7 days of non-dosing), the rats had lost an average of 25 grams (4.7%) of initial body weight (i.e., gained an average of 8 grams since phyto-percolate cessation).

The test animals were observed for adverse reactions immediately after each dose and at 4 and 24 hours subsequent. Daily observation for adverse reactions was continued during the 7 day non-dosing period. Specifically, clinical observations for adverse reactions were made for respiration, motor activity, convulsions, reflexes, ocular signs, salivation, piloerection, analgesia, muscle tone, gastrointestinal effects, and skin/dermal alterations. Gastrointestinal effects were the only observed adverse reaction. Soft to loose stool was observed in all test animals. No other adverse reaction was observed.

TABLE 1

Individual Weight Loss Data

| Test Subject | Pre-dosing Weight (g) | 14 Day Weight (g) | Weight Loss (% Initial Body Weight) | 21 Day Weight (g) | Weight Loss (% Initial Body Weight) |
| --- | --- | --- | --- | --- | --- |
| 1 | 484 | 443 | 41 (8.5%) | 453 | 31 (6.4%) |
| 2 | 482 | 461 | 21 (4.4%) | 479 | 3 (0.6%) |
| 3 | 549 | 521 | 28 (5.1%) | 531 | 18 (3.3%) |
| 4 | 536 | 499 | 37 (6.9%) | 507 | 29 (5.4%) |
| 5 | 510 | 462 | 48 (9.4%) | 468 | 42 (8.2%) |
| 6 | 488 | 459 | 29 (5.9%) | 465 | 23 (4.7%) |
| 7 | 535 | 506 | 29 (5.4%) | 514 | 21 (3.9%) |
| 8 | 586 | 558 | 28 (4.8%) | 562 | 24 (4.1%) |
| 9 | 569 | 504 | 65 (11.4%) | 518 | 51 (9.0%) |
| 10 | 522 | 492 | 30 (5.7%) | 498 | 24 (4.6%) |
| 11 | 556 | 532 | 24 (4.3%) | 537 | 19 (3.4%) |
| 12 | 524 | 503 | 21 (4.0%) | 507 | 17 (3.2%) |
| AVG | 528.4 | 495.0 | 33.4 (6.3%) | 503.3 | 25.1 (4.7%) |

Example 2: Human Weight Loss and Glucose Control Study

A single-center, prospective, randomized, triple-masked, placebo-controlled parallel-group-design pilot clinical trial of the phyto-percolate was performed using two different batches of the phyto-percolate. This trial was conducted in accordance with FDA regulations and under a protocol approved by an Institutional Review Board (IRB).

Subjects:

Primary inclusion criteria were men and women having a body mass index (BMI) of 25-40 m/kg$^2$, 18-70 years old (inclusive), and desirous of losing weight. Major exclusion criteria were moderate to severe co-morbid disease (e.g., cancer); history of stroke, transient ischemic attack (TIA), or similar conditions; uncontrolled hypertension, insulin-dependent diabetes, renal disease, moderately severe cardiac disease, lupus, alcohol abuse, and current or recent use of certain medications including medications and/or supplements for weight loss, glucose management, or arthritis. Women were excluded if they were pregnant, nursing, or actively trying to become pregnant.

Protocol:

Patients were assigned to self-administer one ounce of filtered phyto-percolate or placebo three times each day (t.i.d.) on an empty stomach at least 30 minutes before a meal. Subjects were asked to participate in a reduced carbohydrate diet and light exercise program and complete a one-day-per-week Food Log and a daily Exercise Log for the duration of the clinical trial. Patients were evaluated during a baseline examination and then again at 2-week, 4-week, and 6-week visits. Evaluations included measurement of body weight, arm and waist circumference, and body fat measurements.

Glucose Control Study:

At the baseline examination and at the 4-week and 6-week visits, patients' fasting (12 hour) blood glucose was measured and then their blood glucose was measured one hour after a glucose challenge (25 grams of jelly beans; 90.4% carbohydrate). The difference between the glucose challenge reading and the baseline reading in a single visit is an indicator of the patient's ability to regulate serum glucose levels.

Test Materials:

The patients in the treatment groups were assigned one of two different lots (Batch 1 and Batch 2) of phyto-percolate prepared as described above. The placebo product was similar in appearance (color, viscosity, and odor) to the diluted phytopercolate. All test materials were dispensed in unlabeled blue bottles with instructions to refrigerate after opening.

Enrollment:

A total of 44 subjects were enrolled and randomized for this trial. Ten subjects completed the study on Batch 1 (Cohort 1) of the phyto-percolate and twelve subjects completed Batch 2 (Cohort 2). Seven subjects completed the placebo phase of the trial.

Results:

There were no significant adverse events reported. Patients in the treatment arms of the study reported greater energy and reduced hunger compared to the Placebo group. The remaining results are as follows:

After 2, 4, and 6 weeks of treatment with the diluted filtered phyto-percolate, the average percent total weight loss (above placebo) for all treated patients (Cohorts 1 and 2; n=22) 77.7%, 48.5%, and 68.1%, respectively. After six weeks of phyto-percolate treatment, Cohort 1 lost an average of 106% (9.03 lbs) and Cohort 2 lost an average of 37% (6.01 lbs) more than the weight loss measured in the Placebo group (4.39 lbs).

TABLE 2

Average Weight Loss

| | 2-Week | 4-Week | 6-Week |
| --- | --- | --- | --- |
| Placebo (n = 7) | 2.60 | 3.71 | 4.39 |
| Cohort 1 (n = 10) | 5.71 | 6.81 | 9.03* |
| Cohort 2 (n = 2) | 3.71 | 4.43 | 6.01 | p < 0.10 (unpaired Student's t-test)

TABLE 3

Frequency Distribution of Weight Loss in Individual Patients at 6 Weeks

| Weight Loss | Placebo (number of patients) | Cohort 1 (number of patients) |
| --- | --- | --- |
| >+1 lb. | — | 1 |
| +1 lb. > patient > 1 lb. | — | 1 |
| −1 lb. > patient > −3 lb. | 2 | — |
| −3 lb. > patient > −5 lb. | 2 | — |
| −5 lb. > patient > −7 lb. | 3 | 1 |
| −7 lb. > patient > −9 lb. | — | 3 |
| −9 lb. > patient > −11 lb. | — | 2 |
| −11 lb. > patient > −13 lb. | — | — |
| −13 lb. > patient > −15 lb. | — | — |
| −15 lb. > patient > −17 lb. | — | 1 |

TABLE 3-continued

Frequency Distribution of Weight Loss in Individual Patients at 6 Weeks

| Weight Loss | Placebo (number of patients) | Cohort 1 (number of patients) |
|---|---|---|
| −17 lb. > patient > −19 lb. | — | — |
| <−19 lb. | — | 1* |

*maximum weight loss was 28 lbs.

TABLE 4

Arm and Waist Circumference - Difference Between Baseline and 6 Weeks

| | Placebo | Cohort 1 | Cohort 2 |
|---|---|---|---|
| Arm | 0.083" | 0.41" * | 0.13" |
| Waist | 1.09" | 2.08" ** | 1.34" |

* $p < 0.042$
** $p < 0.21$

TABLE 5

Body Composition - Percent Body Fat: Difference Between Baseline and 6 Weeks

| | Placebo | Cohort 1 | Cohort 2 |
|---|---|---|---|
| Body Fat @ Baseline | 39.1% | 39.2% | 39.0% |
| Improvement in Body Fat (lbs) | 2.11 | 6.03* | 2.89 |
| Improvement in Lean Mass (lbs) | 0.16 | 0.79** | 0.24 |

* $p < 0.01$
** $p < 0.15$

TABLE 6

Frequency Distribution of Body Fat Loss in Individual Patients at 6 Weeks

| Weight Loss | Placebo (number of patients) | Cohort 1 (number of patients) |
|---|---|---|
| >+1 lb. | — | 2 |
| +1 lb. > patient > −1 lb. | 2 | 1 |
| −1 lb. > patient > −3 lb. | 2 | — |
| −3 lb. > patient > −5 lb. | 2 | 2 |
| −5 lb. > patient > −7 lb. | 1 | 2 |
| −7 lb. > patient > −9 lb. | — | — |
| −9 lb. > patient > −11 lb. | — | 1 |
| −11 lb. > patient > −13 lb. | — | — |
| −13 lb. > patient > −15 lb. | — | — |
| −15 lb. > patient > −17 lb. | — | 1 |
| −17 lb. > patient > −19 lb. | — | — |
| <−19 lb. | — | 1 |

* maximum weight loss was 28 lbs.

TABLE 7

Serum Glucose Levels In Individual Patients In Cohort 1 (mg/dl)

| | Baseline | | | 4-Week | | | 6-Week | | |
|---|---|---|---|---|---|---|---|---|---|
| Patient | Fast | Chal. | Diff. | Fast | Chal. | Diff. | Fast | Chal. | Diff. |
| 1 | 158 | 264 | 106 | 155 | 246 | 91 | 152 | 238 | 86 |
| 2 | 72 | 128 | 56 | 89 | 107 | 18 | 80 | 94 | 14 |
| 3 | 75 | 135 | 60 | 87 | 130 | 43 | 91 | 117 | 26 |
| 4 | 73 | 128 | 55 | 78 | 74 | −4 | 76 | 80 | 4 |
| 5 | 105 | 151 | 46 | 104 | 127 | 23 | 103 | 125 | 22 |
| 6 | 139 | 210 | 71 | 129 | 198 | 69 | 126 | 181 | 55 |
| 7 | 145 | 204 | 59 | 124 | 200 | 76 | 132 | 195 | 63 |
| 8 | 85 | 122 | 37 | 74 | 159 | 85 | 83 | 133 | 50 |
| 9 | 91 | 143 | 52 | 91 | 125 | 34 | 92 | 121 | 29 |
| 10 | 78 | 119 | 41 | 92 | 99 | 7 | 88 | 98 | 10 |
| Mean | | | 58.3 | | | 44.2 | | | 35.9 |
| n > 126* | 3 | | | 2 | | | 2 | | |

TABLE 8

Group Mean Data For Glucose Tolerance Test (mg/dl)

| | Baseline | 4-Week | 6-Week |
|---|---|---|---|
| Placebo | 61.7 | 58.3 | 54.0 |
| Improvement | | 3.4 (5.5%) | 7.7 (12.3%) |
| Cohort 1 | 58.3 | 44.2 | 35.9 |
| Improvement | | 14.1 (24.2%) | 22.4 (39.6%)* |
| Cohort 2 | 60.6 | 56.2 | 55.4 |
| Improvement | | 4.2 (6.9%) | 5.2 (8.6%) |

*values > 126 mg/dl are indicative of diabetes.
*$p < 0.08$

Conclusions:

The weight loss, improvement in body fat, improvement in glucose control, as well as energy and hunger categories over the course of this six-week study for those on the phyto-percolate was strong, particularly when compared to the placebo group.

Cohort 1 lost about twice as much weight (1.5 lbs/week) as the placebo group (0.78 lbs/week). Seven of the ten subjects in Cohort 1 lost seven pounds or more, while none of the seven in the placebo group lost that much weight. Correspondingly, a significant reduction in waist size was measured in Cohort 1.

Significant improvements also were measured in the glucose tolerance test. Test subjects demonstrated an average of 2.6× (156%) and 1.7× (69%) improved glucose control at 4 weeks and 6 weeks, respectively, when compared to the placebo group. Furthermore, 6 of the 22 test subjects met the clinically important criterion of >50% control over baseline. Three of these six demonstrated complete control of the glucose challenge, defined as >85% glucose control over baseline.

In Vitro Anti-inflammatory Effects: COX-2 Inhibition

Cyclooxygenase-2 (COX-2) is a key regulator of the inflammatory cascade. COX-2 inhibitors are believed to reduce inflammation by blocking prostaglandin production. In view of the adverse effects associated with mixed COX inhibitors (aspirin, ibuprofen, and naproxen) and the presently available COX-2-specific inhibitors (valdecoxib, celecoxib, rofecoxib), there is a need for improved anti-inflammatory therapies with fewer side effects.

Three separate preparations of the phyto-percolate were screened, using an in vitro assay, for COX-2 inhibition. Riendeau et al., *Can. J. Physiol. Pharmacol.* 75: 1088-1095, 1997; Warner et al., *Proc. Natl. Acad. Sci. USA* 96: 7563-7568, 1999. Briefly, this assay measured to conversion of 0.3 μM arachidonic acid to $PGE_2$ by human recombinant insect Sf21 cells expression human COX-2. The incubation buffer contained 100 mM Tris-HCl (pH 7.7), 1 mM glutathione, 1 μM hematin, and 500 μM phenol. $PGE_2$ was quantified using an enzyme-linked immunoassay (EIA).

Sample 1 was a sample of diluted phyto-percolate concentrated approximately 100-fold by drying under $N_2$. Sample 2 was prepared by drying a 4800 μl sample of diluted phyto-percolate under $N_2$ and reconstituting it in 96

µl of ddH$_2$O just prior to assay. Sample 3 was prepared by lyophilizing a 4800 µl sample of diluted phyto-percolate and reconstituting it in 96 µl of ddH$_2$O just prior to assay. The concentrations of phyto-percolate used, 100×, 10×, and IX, refer to 10 µl, 1 µl, and 0.1 µl of sample, respectively, in a final assay volume of 100 µl. Rofecoxib was used as a positive control for COX-2 inhibition. Each sample was assayed in at least three concentrations and the assays were performed in duplicate.

TABLE 9

COX-2 Inhibition By Phyto-percolate

| Sample | Centration | % COX-2 Inhibition (Individual assay values) | IC$_{50}$ |
|---|---|---|---|
| 1 | 100X | 29 (27, 30.9) | >100X |
|   | 10X  | 11 (9.2, 13.4) |  |
|   | 1X   | −4 (−9.0, 0.3) |  |

TABLE 9-continued

COX-2 Inhibition By Phyto-percolate

| Sample | Centration | % COX-2 Inhibition (Individual assay values) | IC$_{50}$ |
|---|---|---|---|
| 2 | 100X | 61 (66.7, 56.1) | 46.5X |
|   | 10X  | 27 (23.7, 30.5) |  |
|   | 1X   | 20 (13.3, 27.6) |  |
| 3 | 100X | 58 (63.9, 52.3) | 61.9X |
|   | 10X  | 24 (21.7, 26.0) |  |
|   | 1X   | 18 (13.3, 23.1) |  |
| rofecoxib | 1 µM | 88 (90.1, 85.6) | 0.198 µM |
|   | 0.3 µM | 55 (58.8, 51.8) |  |
|   | 0.1 µM | 33 (34.7, 31.5) |  |
|   | 0.03 µM | 16 (22, 10.5) |  |
|   | 0.01 µM | 11 (8.2, 14) |  |

In Vivo Anti-Inflammatory Effects: Carageenan-Induced Paw Edema

The carrageenan-induced paw edema assay was used as an in vivo indicator of the anti-inflammatory effects of the phyto-percolate. Carrageenan induces local inflammation and edema when injected into the paw pad of a rat (Di Rosa et al., 1971). The development of paw edema is believed to be biphasic (Vinegar et al., 1969). The initial phase is attributable to the local release of histamine and serotonin (Crunkhon et al., 1971) and the second phase is caused by prostaglandin release as a result of COX activation. The second phase is measured as an increase in paw volume and has been demonstrated to be responsive to steroidal and non-steroidal anti-inflammatory agents.

Groups of test subjects (n=6) received oral doses of either vehicle control (water; 5 ml/kg), indomethacin (30 mg/kg), aspirin (100 mg/kg), unfiltered phyto-percolate (10 ml/kg), or filtered phyto-percolate (10 ml/kg) 30 minutes prior to intraplantar administration of carrageenan (0.1 ml of a 1% solution). Paw volume was measured at 0, 2, 4, 6, 8, and 20 hours after treatment using a plesthysmometer to measure volume displacement. Each treatment group is compared to control.

As shown in Table 10, the paw volume of the control animals and all treatment groups nearly doubled in two hours and remained so through the four hour time point. By six hours, paw volume was reduced by 30% and 50% in the groups administered the filtered and unfiltered phyto-percolate, respectively. This reduction in edema was significantly better than that observed for either the indomethacin or the aspirin groups at this time. Further, the reduction in edema measured for the two phyto-percolate groups was comparable to both the indomethacin and aspirin groups at the 8 hour and 20 hour time points.

TABLE 10

In Vivo Anti-inflammatory Effects of Phyto-percolate
Mean paw volume (ml) ± SD (% change from control)

| Group | 0 hours | 2 hours | 4 hours | 6 hours | 8 hours | 20 hours |
|---|---|---|---|---|---|---|
| Control | 1.24 ± 0.17 | 2.18 ± 0.24 | 2.17 ± 0.27 | 2.12 ± 0.15 | 2.05 ± 0.08 | 1.85 ± 0.08 |
| Indomethacin | 1.25 ± 0.05 (1%) | 2.25 ± 0.23 (7%) | 2.18 ± 0.22 (1%) | 2.00 ± 0.22 (−12%) | 1.83 ± 0.23 (−22%) | 1.37 ± 0.10 (−38%) |
| Aspirin | 1.25 ± 0.08 (1%) | 2.22 ± 0.28 (4%) | 2.07 ± 0.23 (−10%) | 1.92 ± 0.18 (−20%) | 1.80 ± 0.18 (−25%) | 1.42 ± 0.16 (−23%) |
| Filtered | 1.22 ± 0.04 (−2%) | 2.15 ± 0.10 (−3%) | 2.15 ± 0.10 (−2%) | 1.78 ± 0.10 (−34%) | 1.78 ± 0.10 (−27%) | 1.35 ± 0.08 (−30%) |
| Unfiltered | 1.20t 0.13 (−4%) | 2.15 ± 0.12 (−3%) | 2.13 ± 0.10 (−4%) | 1.67 ± 0.10 (−45%) | 1.67 ± 0.10 (−38%) | 1.28 ± 0.12 (−37%) |

Immunological Effects: Rodent Model of HIV Infection

The effect of treatment using the phyto-percolate was investigated using a rat model of HIV infection. The HIV model used inoculates rats with seven (7) of the nine (9) HIV genes, making it a non-contagious model that develops full symptoms of HIV by 9 months after inoculation, with a life expectancy of 12 months.

Some of the most devastating symptoms of HIV manifest themselves in the liver and the immune system. Liver problems are frequent causes of illness and death in people with HIV infection. Throughout the study, liver function tests including AST, ALT, GGTP, bilirubin, and albumin were monitored in the treatment and control groups. C-reactive protein was assayed as an inflammatory marker. The immune response was monitored using IgG, IgA, and IgM levels which are known to decline during the progression of AIDS.

For testing, serum was drawn by cardiac puncture for baseline (pre-inoculation) values. The treatment group received diluted phyto-percolate for their drinking water, which was allowed ad libitum, while the control group received filtered water. Serum was drawn by cardiac puncture, as above, every thirty (30) days until the termination of the study.

After 60 days of treatment with the diluted phyto-percolate, the treatment group had an average 30% increase in IgA levels, 50% increase in IgG levels, and a 40% reduction in C-reactive protein (C-RP) levels, relative to the untreated group (Table 11). No significant differences in body weight, average daily food consumption, or average daily liquid consumption were detected between the groups

TABLE 11

Serum Analysis From Rat HIV Study

| Animal Group | AST (U/L) | ALT (U/L) | Bilirubin (mg/dL) | C-RP (mg/ml) | IgG (mg/dL) | IgM (mg/dL) | IgA (mg/dL) |
| --- | --- | --- | --- | --- | --- | --- | --- |
| Control | | | | | | | |
| Base | 117 | 70 | 0.07 | 3.41 | 57 | 27 | 18 |
| 1 Mo. | 95 | 60 | 0.12 | 0.65 | 69 | 26 | 24 |
| 2 Mo. | 122 | 67 | 0.12 | 0.93 | 120 | 26 | 24 |
| HIV | | | | | | | |
| Base | 116 | 77 | 0.07 | 3.37 | 60 | 26 | 21 |
| 1 Mo. | 166 | 76 | 0.21 | 0.58 | 108 | 27 | 25 |
| 2 Mo. | 139 | 81 | 0.13 | 0.56 | 167 | 23 | 38 |

Administration of Phyto-Percolate

The phyto-percolate dosage will vary with the severity of the disease, the biochemical activity of the disease, and the age and weight of the subject. The effects of using the phyto-percolate will be measured using standard parameters known in the art for any such disease state.

In one embodiment, the phyto-percolate is orally administered as a liquid. As described in several of the foregoing examples, the phyto-percolate is diluted in filtered water to about 50 ppm of the protein species of the 67.5 kDa peak measured by HPLC and UV detection (described above). However, depending upon the severity of disease or desired clinical outcome, the concentration of phyto-percolate (and hence the dosage for the protein species) may be altered. For example, the protein species may be present in the orally administered liquid in concentrations including about 100 ppm, 250 ppm, 500 ppm, 750 ppm, 1000 ppm, 1500 ppm, or more. It is also contemplated that the protein fraction is isolated from the phyto-percolate and formulated for parentera administration (e.g., intravenous, intramuscular, and subcutaneous injection, topical, rectal or vaginal administration or other).

In an adult subject, the dosage of diluted phyto-percolate will vary from about one ounce per day, generally on an empty stomach, such as for maintenance and the retardation of aging, to about an ounce every hour, up to about 12 ounces per day, in a hospitalized burn or accident case, or during the chemotherapy infusion. The controlled diabetic or cardiovascular subject is generally treated at about two to three ounces of phyto-percolate per day. Dosing on an empty stomach is noted because of the potential for interference on phyto-percolate function from food-stimulated gastrointestinal activities. A 50-70 lb. child is dosed at about three to four ounces per day, generally dosing on an empty stomach, during an acute infection. The greater the free radical oxidative tissue destructive activity caused by age or disease state, the greater the recommended dosage of the phyto-percolate. Without being bound to any particular theory, it is thought that the intake of phyto-percolate per day is more directly related to the severity of oxidative tissue destruction than to the weight of the subject.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. Likewise it should be understood that the phyto-percolate can be used to enhance the well being and performance of animals.

According to other various exemplary embodiments of the present invention, the present invention comprises administering a composition to affect various cytokines and NF-κB. The composition has been described in numerous commonly owned and co-pending patent applications including U.S. Pat. No. 7,807,622 entitled "Composition and Use of Phyto-Percolate For Treatment of Disease," U.S. patent application Ser. No. 12/897,574 entitled "Composition and Use of Phyto-Percolate For Treatment of Disease," U.S. patent application Ser. No. 11/587,266 entitled "Method of Preparation and Use of Fibrinolytic Enzymes in the Treatment of Disease," U.S. Patent Application Ser. No. 61/306,591 entitled "Method of Lowering Cholesterol With PAZ Components," and U.S. Patent Application Ser. No. 61/311,838 entitled "Agents and Mechanisms for Treating Hypercholesterol with PAZ Components," all of which are herein incorporated by reference in their entirety. All foreign and PCT patent applications claiming priority to these U.S. applications are also incorporated herein by reference in their entirety.

As noted above, the composition referred to herein as "phyto-percolate" is a non-toxic composition comprised generally of molecules produced by the culture or co-culture of specific microorganisms such as algae, moss, bacteria, and fungi. In one exemplary embodiment, a deposit of the culture used to create phyto-percolate has been placed in the American Type Culture Collection, of Manassas, Va. as Deposit No. PTA-5863. This deposit is available to the public upon grant of a patent disclosing same. This deposit was made pursuant to 37 C.F.R. § 1.808 and MPEP § 2410.01 and therefore, access to the deposit will be available during pendency of this application making reference to the deposit to one determined by the Commissioner to be entitled thereto under 37 C.F.R. § 1.14 and 35 U.S.C. § 122 and with one exception, that all restrictions imposed by the depositor on the availability to the public of the deposited biological material be irrevocably removed upon granting of the patent.

In one exemplary embodiment, the composition described herein as "phyto-percolate" is created by the process set forth below. According to this embodiment, approximately one or more aliquots of the culture of the type currently on deposit as ATCC culture deposit number PTA-5863 are first obtained. In various embodiments where more than one aliquot is used, the aliquots may be combined in one larger composite culture vessel and maintained using the methods set forth below.

According to this exemplary embodiment, for each aliquot of culture obtained and cultured successfully from cryopreservation, the total volume is diluted using sterile deionized water to approximately 10 mL total volume (for example, 3 aliquots (~4.5 mL) are combined and diluted to 30 mL total volume). Further, a nutrient blend stock solution is prepared by mixing approximately 20 mg of dry active baker's yeast in approximately 1 mL warm sterile deionized water and then incubated for approximately 20 minutes at room temperature, yielding enough nutrient for approximately 1000 culture aliquots. Then, approximately 1 uL of the prepared nutrient blend is added to each diluted aliquot (for example, to 3 combined and diluted aliquots, add 3 uL prepared nutrient blend) and the mixture is then swirled gently.

The next step of producing phyto-percolate according to this exemplary embodiment comprises the step of incubating the culture sample with nutrient blend for approximately 1 week at room temperature in a sterilized culture vessel such as a round-bottom glass culture vessel with an ambient sterile-filtered air vent. In this exemplary embodiment, the mixture is swirled once half way through the week and maintained under approximately a 12:12 hour cycle of simulated daylight. After this week, approximately 1 uL freshly prepared nutrient blend is added to the culture vessel for approximately each diluted aliquot used and this new mixture is preferably swirled gently. The culture sample with nutrient blend is incubated for approximately one additional week at room temperature and preferably swirled once half way through the week and maintained under a 12:12 hour cycle of simulated daylight.

Continuing with this exemplary method of producing phyto-percolate, the liquid volume is slowly drawn off or harvested using a sterile tubing and siphon or peristaltic pump from approximately the top half of the culture vessel without disturbing the algal biomass growing in the bottom of the culture vessel, yielding approximately 5 mL per deposit aliquot used. The liquid may be reserved in a sterile glass storage container or another appropriate storage container, sterile-filtered and administered as desired. The liquid volume in the culture vessel should be replenished back to approximately its pre-harvested volume using sterile deionized room temperature water allowing the total final volume to be approximately 10 mL per deposit aliquot used. Approximately 1 uL of freshly prepared nutrient blend is then added to the culture vessel for approximately each aliquot used and then the mixture is swirled gently and allowed to incubate as described above in subsequent cycles as desired.

With continued reference to this exemplary embodiment, the culture sample and nutrient blend is incubated for approximately 1 week or more at room temperature while maintaining approximately a 12:12 hour cycle of stimulated daylight. While this culture is incubating with the nutrient blend, the previously harvested material is filtered through sterilizing membrane filters (or similar filters as those skilled in the art will recognize) with approximately a 0.2 um pore size to generate the final bioactive liquid, described herein as 'composition' or 'phyto-percolate'. Any biomass captured in the filter may be destroyed or collected. Supplemental micronutrient or trace mineral blends specific to the needs of the culture may also be added to the culture during incubation or scale-up to preserve the integrity of the original culture biomass and support further growth.

Further, according to this exemplary manufacturing method, once sufficient biomass has been generated over time in the culture (approximately 8 to 12 weeks or more), the culture may be split into 2 equal cultures as needed in a scale-up process by the following exemplary steps. First, homogenize the culture gently to fully suspend the biomass. Second, transfer approximately half of the homogeneous culture into a new sterilized glass or other appropriate culture vessel. Third, replenish the liquid volume in each of the two culture vessels back to original culture volume using sterile deionized water at room temperature. Fourth, add approximately 1 uL of freshly prepared nutrient blend to each culture vessel and swirl gently. Fifth, incubate the cultures with nutrient blend for approximately 1 week at room temperature, preferably swirling once half way through the week and maintaining them under the approximate 12:12 hour cycle of simulated daylight. Sixth, add approximately an additional 1 uL freshly prepared nutrient blend to the culture vessel. Seventh, incubate the culture sample with nutrient blend for approximately an additional week at room temperature, preferably swirling once halfway through the week. Finally, with respect to this scale-up process, it should be noted that multiple cultures can be combined in larger culture vessels and maintained using the same general culturing methods and nutrient-to-culture volume ratios.

With continued reference to this exemplary embodiment of producing phyto-percolate, the steps noted above should be proceeded as needed to generate a sufficient amount of phyto-percolate and its various derivatives. A sample of the phyto-percolate sold under the trademark PROALGA-ZYME® may also be obtained from Health Enhancement Products, Inc. of Bloomfield Hills, Mich.

It should be noted that while specific examples have been given related to a method of producing a composition and quantities in the composition, that various modifications to the compositions and methods of producing the composition can be used and fall within the scope of the present invention. Further, it is contemplated and within the scope of the present invention that other culture methods, dilution volumes, growth media or nutrient blends, volumes or feeding frequencies, incubation times, culture vessels, harvesting or filtering methods, etc. may also be used to produce phyto-percolate and the exemplary method noted above is not intended to exclude other methods of producing phyto-percolate.

As used herein, the term phyto-percolate denotes the composition described above and derivatives thereof. Phyto-percolate also denotes any composition that is made with the process described above or variations to that process that would be recognizable to one of ordinary skill in the art. Applicants reserve the right to more narrowly define the term "phyto-percolate" after this application has been filed.

Further, according to various exemplary embodiments of the present invention, the phyto-percolate is isolated into various fractions. Certain exemplary, non-limiting processes are described below.

Figure 13:
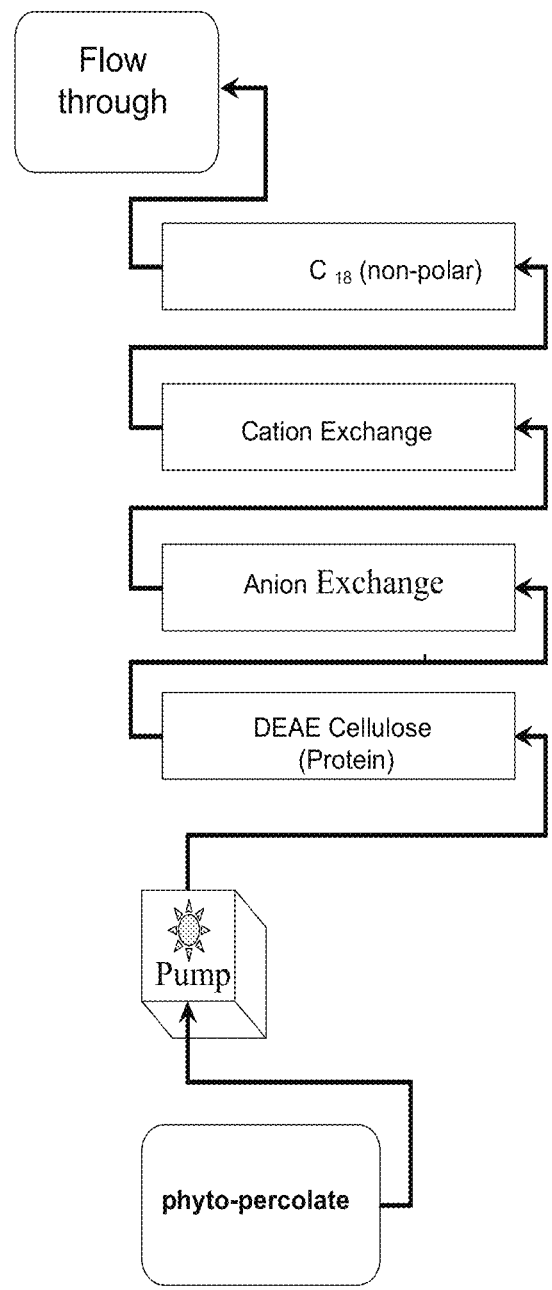
FIG. 13 provides an exemplary flow chart for the separation and isolation of the constituents.

According to one exemplary embodiment, the phyto-percolate is passaged in series through four chromatography columns with the dimensions of 2.7 cm×23 cm (approximately 100 mL of resin at full capacity each) at a flow rate of approximately ~6 mL per minute using a pump such as a peristaltic pump. The rate is selected for optimal binding, and is also based on the flow rate of the slowest resin, (C18). The process is optimized to enable the fractionation of approximately 180 L of phyto-percolate. Other variations and modifications of these methods, including optimization of the process to accommodate other sample volumes, will be apparent to those of ordinary skill in the art. FIG. 13 provides an exemplary flow chart for the separation and isolation of the constituents.

Following passage of approximately 18 L through a resin, such as a DEAE resin, the column is replaced with a fresh column and the bound material from the prior approximate ~18 L immediately eluted, filtered through a 0.2-micron filter and the eluates stored in sterile containers. Similarly and according to this exemplary embodiment, the anion and cation exchange resins are replaced after the passage of approximately ~36 L of material through each. A single hydrophobic resin, (C18), is used for the entire process. All eluted fractions from the first three columns are immediately passaged through sterile filters and stored in sterile containers. Elution of the material bound to the C18 column requires the use of organic solvents, which are subsequently removed as detailed below. The material that does not bind to any of the four columns, having been depleted of the majority of the organic constituents, is labeled as the "flow-through" fraction and is collected into sterile containers for subsequent testing and use.

A detailed description of each step in the separation process is now described according to one exemplary embodiment of the present invention. First, the chromatography column resins are prepared by following the following process. DEAE Cellulose (weak anion exchange resin widely used for isolation of proteins) is used in this exemplary process. Prior to use, DEAE cellulose must be pretreated with a strong base and acid solutions to strip off any contaminants that might interfere with the binding of proteins or contaminate the proteins thus isolated. Approximately twenty grams of DEAE-cellulose are rehydrated in approximately ~300 mL of water (ultrapure water is used in this exemplary embodiment) and allowed to swell overnight or an equivalent time at room temperature in a 1 L flask. Water is decanted from the settled/packed resin and the resin is resuspended in an additional ~300 mL of water such as ultrapure water. This resuspension and decanting procedure is repeated two more times through the course of approximately twenty-four hours. The washed resin is resuspended in ~200 ml of 0.1 M NaOH/0.5 M NaCl then transferred to a 600 ml Buchner funnel according to this exemplary embodiment. The flask is then rinsed with an additional approximate 50 ml of 0.1 M NaOH/0.5 M NaCl and the material suspended in the rinse is also transferred to the funnel. The resin is allowed to sit in this solution for ~10 minutes before allowing the solution to flow through by gravity. The resin is then rinsed with an additional ~750 ml of 0.1M NaOH/0.5 M NaCl. This filtering procedure is then repeated using 0.5 M NaCl and again using 0.1 M HCl/0.5 M NaCl. The resin is initially rinsed with ~2 L water such as ultrapure water followed by a further rinsing with ~5 L of ultrapure water until the pH of the effluent is greater than five. The DEAE-cellulose slurry is then transferred to five columns (according to this exemplary embodiment, the five columns measure 2.7×23 cm) and allowed to settle. The packed columns have bed volumes of ~100 ml and are stored at 4° C. until use in this exemplary embodiment.

Further, according to this exemplary embodiment, approximately 100 g of a dry resin such as BioRad AG 1-X8 Strong Base Anion Exchange Resin: Catalogue number 140-1441, received in chloride form, 100-200 dry mesh, 106-180 μm wet bead diameter, quaternary ammonium functionality, is used. To remove any unwanted oxidation contaminants, the resin is exhausted by first hydrating it with deionized water and then loading the beads into a glass column equipped with a glass filter at the bottom of each column. By passing approximately 500 mL of 1.0 M sodium chloride solution through the resin over a period of about three hours, the resin swells and releases any unwanted oxidation products. This process also converts the resin to a chloride (Cl—) form. After this salt treatment, the resin is rinsed with approximately two liters of deionized water to remove excess sodium chloride.

The anion exchange resin, now completely in the chloride (Cl—) form, is converted into the hydroxide (—OH) form by passing approximately 500 mL of 2.0 M sodium hydroxide solution through the column over a period of about two hours. The resin is subsequently rinsed with approximately 7.0 L of deionized water, overnight, using a gravity siphon drip as the effluent may be slightly off-color and have an ammonia-like odor. Following this step, the resin's effluent is clear, colorless, and odorless in this exemplary embodiment. The solution eluting from the column is pH neutral as measured with indicating strips. This anion exchange resin is now considered to be regenerated and ready for use.

Further, according to this exemplary embodiment, approximately 100 g of a dry resin such as DOWEX MONOSPHER® 88 Strong Acid Cation Exchange Resin: 400-700 μm bead diameter with sulfonate functionality available from the Dow Chemical company of Midland, Mich. is used. As for the anion exchange resin, unwanted oxidation contaminants are exhausted by first hydrating with deionized water and then loading the beads into a glass column equipped with a glass filter at the bottom of each column. Passage of approximately 500 mL of 1.0 M sodium chloride solution through the resin over a period of about three hours releases any unwanted oxidation products and removes any ions that may have been on the resin from production. The sodium chloride exhaustion causes the resin to convert completely to the sodium (Na+) form. After this salt treatment, the resin is rinsed with approximately 2.0 liters of deionized water to remove excess sodium chloride.

The cation exchange resin, now completely in the sodium (Na+) form, is converted to the acid (H+) form by passing approximately 500 mL of 2.0 M hydrochloric acid solution through the column over a period of about two hours. The resin is subsequently rinsed with ca. 3.0 L of deionized water, until the solution eluting from the column is pH neutral as measured with indicating strips. This cation exchange resin is now considered to be regenerated and ready for service.

Further, and in accordance with this exemplary embodiment, at the silica gel 90 C18-Reversed phase (C-18), approximately 25 g of resin is resuspended in ultrapure water, packed into a column and washed with approximately 5 volumes of water prior to use.

Continuing on with the description of this exemplary embodiment, the following paragraphs provide a detailed timetable for the fractionation process. The phyto-percolate is pumped through columns set up in sequence such that the effluent from one column flows through to the next column, at a flow rate of approximately 6.9 ml/min. Additionally, collection vessels are cleaned and dried for flow-through collection. The saved flow-through is passaged through a 0.2 μm filter system and is stored at approximately 4-25° C.

After the first ~18 L that passes through, the DEAE-cellulose column is removed and eluted with 250 ml 1M NaCl, pH 8.3. The eluate is filtered through a 0.2μ filter, labeled and stored at 4° C. Then, a fresh DEAE-cellulose column is placed into the fractionation system and the process resumed. After another ~18 L are passaged, the DEAE-cellulose, anion exchange, and cation exchange columns are removed and each eluted with approximately 250 ml 1M NaCl, pH 8.3. The eluates are passaged through individual 0.2 μm filter systems, labeled and stored at approximately 4° C.

According to this exemplary embodiment, fresh DEAE-cellulose, anion exchange and cation exchange columns were placed into the fractionation system and the process resumed. After another ~18 L, the DEAE-cellulose column is removed and eluted with 250 ml NaCl, pH 8.3. The eluate is passaged through a 0.2 μm filter system, labeled and stored at 4° C. Elution of material bound to the C18 column (from all material): The C-18 column is drained of excess water and purged with compressed nitrogen to remove residual water.

The column is then flushed with approximately 50 mL of acetone to remove the last traces of water and organics, followed by approximately 50 mL of ethyl acetate and finally approximately 50 mL of hexanes. The solution is then dried with excess anhydrous magnesium sulfate and filtered through glass wool or another similar material.

The solvent is then removed with a stream of nitrogen, and then reconstituted with approximately 5 mL of ethyl acetate and transferred to a glass vial of known mass. The solvent is removed with nitrogen and the final mass is taken.

Further, the DEAE-cellulose, anion exchange, and cation exchange columns were each eluted with approximately 250 ml 1M NaCl, pH 8.3. The eluates were passaged through individual 0.2 μm filter systems, labeled and stored at approximately 4° C. One mL of eluate from the cation exchange column (labeled as Fraction 3 or "F3" in FIGS. 1-8 and described in the present invention) is the eluate captured from the cation exchange columns after the phyto-percolate has passed through the first three columns using the methods described above and is approximately 160 fold concentrated compared to the unseparated phyto-percolate introduced into the separation process (i.e. for every 160 mL of phyto-percolate introduced into the process, one mL of eluate was isolated in PF3).

Fraction 4 as labeled as F4 in FIGS. 5-12 and described in the present invention is the flow-through captured at the end of the fractionation series after the phyto-percolate has passed through all 4 columns using the methods described above.

In the experiments for which results are presented in FIGS. 5-12, the dilutions provided are those of the completed, unseparated phyto-percolate composition or of the specific fractions identified. For example, since the total volume of flow-through isolated in F4 is identical to that of the unfractionated phyto-percolate, the relative concentration(s) of all constituents in F4 was identical to that of the unseparated phyto-percolate, whereas the relative concentration of constituents in a 1:20 dilution of the F3 fraction eluted from the strong cation exchange resin is approximately 8 fold concentrated relative to unseparated phyto-percolate (since one mL of F3 is obtained for every 160 mL of phyto-percolate, a 1:20 dilution equates to the constituents therein being approximately 8 fold concentrated relative to unseparated phyto-percolate).

According to this exemplary embodiment, phyto-percolate and the flow-through/F4 were tested as they appeared in their original concentrations right off the columns, only diluted 1:20 and 1:100 as described herein. The culture of peripheral blood mononuclear cells ("PBMC") is prepared with two vials of frozen PBMCs that were obtained from normal healthy human subjects by a commercial vendor and were added to 2×10 ml medium and centrifuged. PBMCs were resuspended and cultured in RPMI1640/5% FBS for 24 h. (1 vial of frozen cells in 11 ml medium).

Treatment agents for this exemplary method comprise three agents: unseparated phyto-percolate ('PAZ'), fraction 3 ('F3'), fraction 4 ('F4'). Treatment concentration for each was 1:20 & 1:100. An exemplary sample preparation method for each agent by dilution is as follows: First, a 1:10 dilution is prepared by combining 0.7 ml agent (either PAZ, F3 or F4)+6.3 ml RPMI1640/5% FBS to obtain a total volume of 7 ml of a 1:10 solution. Second, a 1:50 dilution is prepared by combining 1.2 ml of the 1:10 dilution (of each respective agent)+4.8 ml RPMI1640/5% FBS for a total volume of 6 ml of 1:50 solution. In addition, for diluted fraction 3 (F3), 1M NaOH was used to adjust pH to 7.0.

According to this exemplary embodiment, seeding, treatment, and detection is accomplished by the following steps. Two dishes of PBMCs were combined and the small amount of PBMCs was stained with 0.4% Trypan blue and the cell number of PBMCs was counted using known techniques.

In this embodiment, an enzyme linked immunosorbent assay ("ELISA") analysis of inflammatory cytokine secretion, a protocol provided in a commercial kit for the parallel quantification of the production of human cytokines was employed. The PBMC were first seeded into a twenty-four well plate (337,600 cells/each well in 320 μl medium) and incubated at 37° C. for forty-eight hours. In this exemplary embodiment, an additional 320 μl of culture medium was added, and cells were cultured for 48 hours. For the control cultures, the 320 μl of additional medium contained no additional components. To stimulate the production of several cytokines, parallel cultures of PBMC were treated with 50 ng/ml phorbol myristate acetate ('PMA') and 1 μg/ml ionomycin for 24 hr, followed by addition of 0.64 μl PMA/0.64 μl ionomycin and incubation for an additional twenty-four hours. For cultures in which PBMC were treated with phyto-percolate or fractions derived therefrom, the 320 μl of additional medium which contained 1:10 or 1:50 dilutions of phyto-percolate or fractions 3 or 4 derived therefrom (to yield final dilutions in the cultures of 1:20 or 1:100) was added just before incubation for 24 hr, and then incubated with or without PMA+ionomycin treatment for an additional 24 hours. Duplicate PBMC cultures were examined for each of these conditions. At the end of the incubation period, the cultures were centrifuged and the supernatant medium was collected and aliquots stored at ~70° C. The quantity of cytokines present in each of the culture medium samples was subsequently determined using a Multi-Analyte ELISArray Kit (product number MEH-004A) for human inflammatory cytokines and methods provided by SA Biosciences.

Analysis of the effect of phyto-percolate or fractions isolated therefrom on the DNA-binding activity of NF-κB in the nuclear protein fractions of the cultured PBMC was determined as follows in this exemplary embodiment: approximately 18.26 mL of suspended PBMC were added to approximately 18 mL of culture medium and 2 mL of this cell suspension (2,718,000 cells in 2 mL) were seeded into each 60 mm culture dish. In this exemplary embodiment, an additional 2 mL of culture medium was added. For the control cultures, the 2 mL of additional medium contained no additional components. Culture of cells stimulated with TNF-α was performed identically, including addition of 2 mL of additional medium at the start of the culture, but 2 μL of TNF-α (50 ng/ml) was added to these cultures one hour before harvesting. For cultures in which PBMC were treated with phyto-percolate or fractions derived therefrom, the 2 mL of additional medium contained 1:10 or 1:50 dilutions of phyto-percolate or fractions 3 or 4 derived therefrom (to yield final dilutions in the cultures of 1:20 or 1:100) was added just before incubation. Two positive controls for the inhibition of the DNA binding activity of NF-κB were performed. In one case, PBMC were cultured for 24 h in the presence of 25 μM G2535 for 24 h followed by TNF-α treatment for 1 h. In the second case, PBMC were cultured for 24 h in the presence of 25 μM Genistein for 24 h followed by TNF-α treatment for 1 h. Duplicate PBMC cultures were examined for each of these conditions which were then cultured at 37° C. for 24 hr before harvesting.

At the end of the incubation period, nuclear proteins were extracted from the cells according to the method of set forth in PubMed—Cancer Research 65:6934, 2005 and electrophoretic mobility shift assays ("EMSA") were performed for the binding of NF-κB to a synthetic radiolabeled DNA sequence corresponding to the cognate NF-κB DNA-binding element using an established protocol such as the one set forth in PubMed—Cancer Research 65:6934, 2005.

Turning now to FIGS. 5-12, the methods of effecting various cytokines and NF-κB with the phyto-percolate, which is denoted by the phrase "PAZ", and fractions thereof are discussed according to certain exemplary embodiments of the present invention. Although specific examples of the composition effecting the production of various cytokines and the DNA-binding activity of NF-κB are discussed herein, the present invention is not limited to only those examples or the compositions and quantities, dilutions, or fractions of the compositions discussed herein although Applicants reserve the right to claim certain quantities, dilutions, or fractions at a later date.

With specific reference to FIGS. 5A-5D, raw data is shown from various electrophoretic mobility shift assays or ("EMSA") for NF-κB performed using a deoxyoligonucleotide corresponding to the DNA sequence to which NF-κB binds, labeled with an infrared dye. Specifically, FIGS. 5A and 5B depict both results in "low density" in which the bands were visualized using an infrared scanner (Li-Cor Corporation) for a short period of time (FIG. 5A) and in "high density" in which image obtained from the same gel was enhanced (FIG. 5B). FIGS. 5C and 5D depict the results when the tests resulting in the assays shown in FIGS. 4A and 4B were re-run for a longer time period (three hours compared to two hours) using an identical amount of the nuclear protein.

Figure 6:
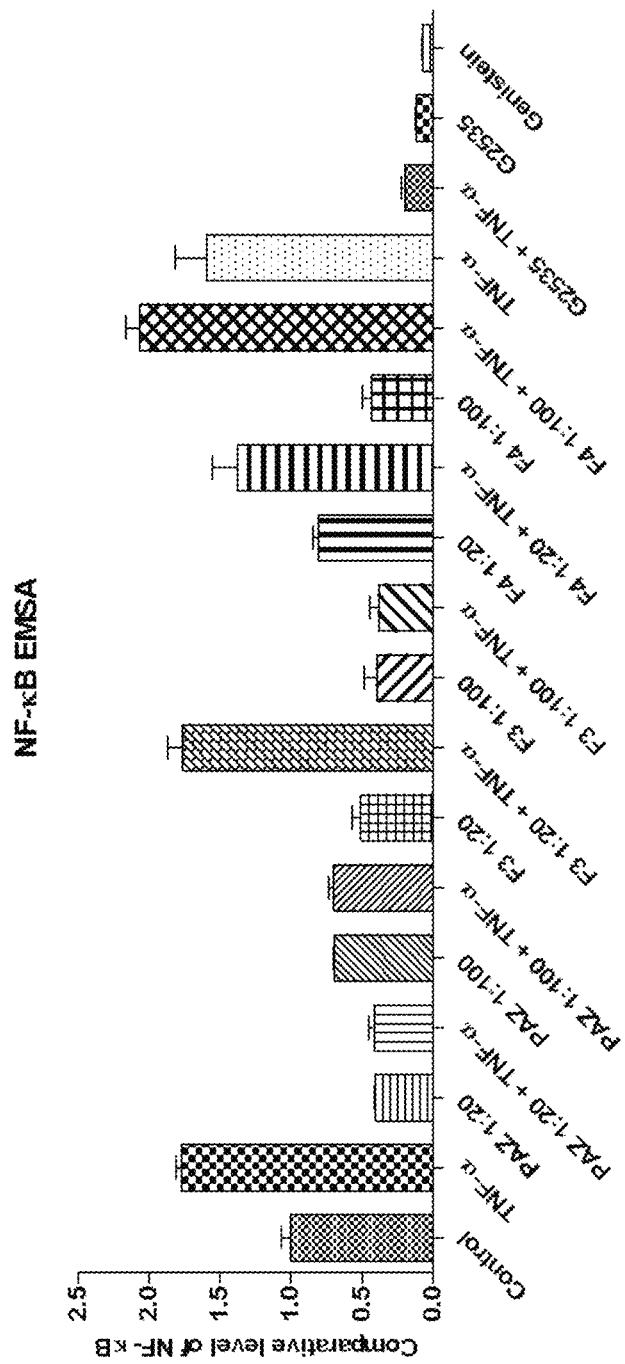
FIG. 6 shows a bar graph illustrating the quantitative analysis of the results obtained in the experiment presented in FIGS. 1A-1D, thus illustrating the efficacy of the method effecting NF-κB according to various exemplary embodiments of the present invention.

Turning now to FIG. 6, the effects of administering phyto-percolate, as well as various fractions that were obtained by chromatographic treatment of the complete phyto-percolate composition, on the DNA-binding activity of NF-κB in PBMC with or without stimulation with phorbol myristate acetate (PMA) are shown according to certain exemplary embodiments of the present invention. Active NF-κB is a dimeric protein that binds to a cognate DNA sequence to control the transcription of specific proteins that play key roles in inflammation. Therefore, the more NF-κB that is expressed and that binds to DNA, the greater the amount of inflammatory proteins that will be produced and the greater the inflammatory response. Reducing the overall amount of NF-κB that binds to DNA sequence of NF-κB target genes lowers the inflammation as well as reduces the other effects of NF-κB such as reducing the activation of various viruses such as the HIV virus.

As shown in FIG. 6, control, unstimulated and untreated PBMC were tested to determine the native amount of NF-κB that binds to a radiolabeled DNA probe. This represents a baseline measurement of NF-κB activity that is expressed as a relative unit of 1.0. According to this example, when tumor necrosis factor alpha or TNF-α was added, the DNA-binding activity of NF-κB was significantly increased to a relative level of almost 2.0. However, when a composition comprised of 1:20 dilution of phyto-percolate (labeled 'PAZ') was added to the PBMC, the concentration of NF-κB decreased significantly compared to the control to a relative level of approximately 0.4 units. As depicted in FIG. 6, and according to various exemplary embodiments of the present invention, phyto-percolate in a 1:20 and 1:100 dilution when combined with TNF-α, phyto-percolate in a 1:100 dilution alone, fractions 3 and 4 (labeled "F3" and "F4") alone in a 1:20 and 1:100 dilution, and fraction 3 in a 1:100 dilution in the presence of TNF-α, reduced the overall concentration of NF-κB compared to the control, whereas fraction 4 in 1:100 dilutions plus TNF-α increased NF-κB concentration. FIG. 6 also depicts the results of adding TNF-α, G2535 plus TNF-α, G2535 alone, and genistein alone. As shown in FIG. 6, phyto-percolate alone, fraction 3 and fraction 4 inhibited NF-κB and both phyto-percolate and fraction 3 inhibited TNF-α induced activation of NF-κB.

Therefore, administering phyto-percolate may decrease the DNA-binding activity of NF-κB which in turn reduces inflammation. Further, since NF-κB activation promotes the replication and/or function of certain viruses, such as the HIV virus, reducing the total DNA-binding activity of NF-κB may reduce or prevent the pathological effects of certain viruses, such as HIV. The present invention contemplates that any effects of reduced DNA-binding activity of NF-κB now known or discovered in the future can be achieved by administering an effective amount of phyto-percolate and dilutions, fractions and derivatives thereof.

Figure 7:
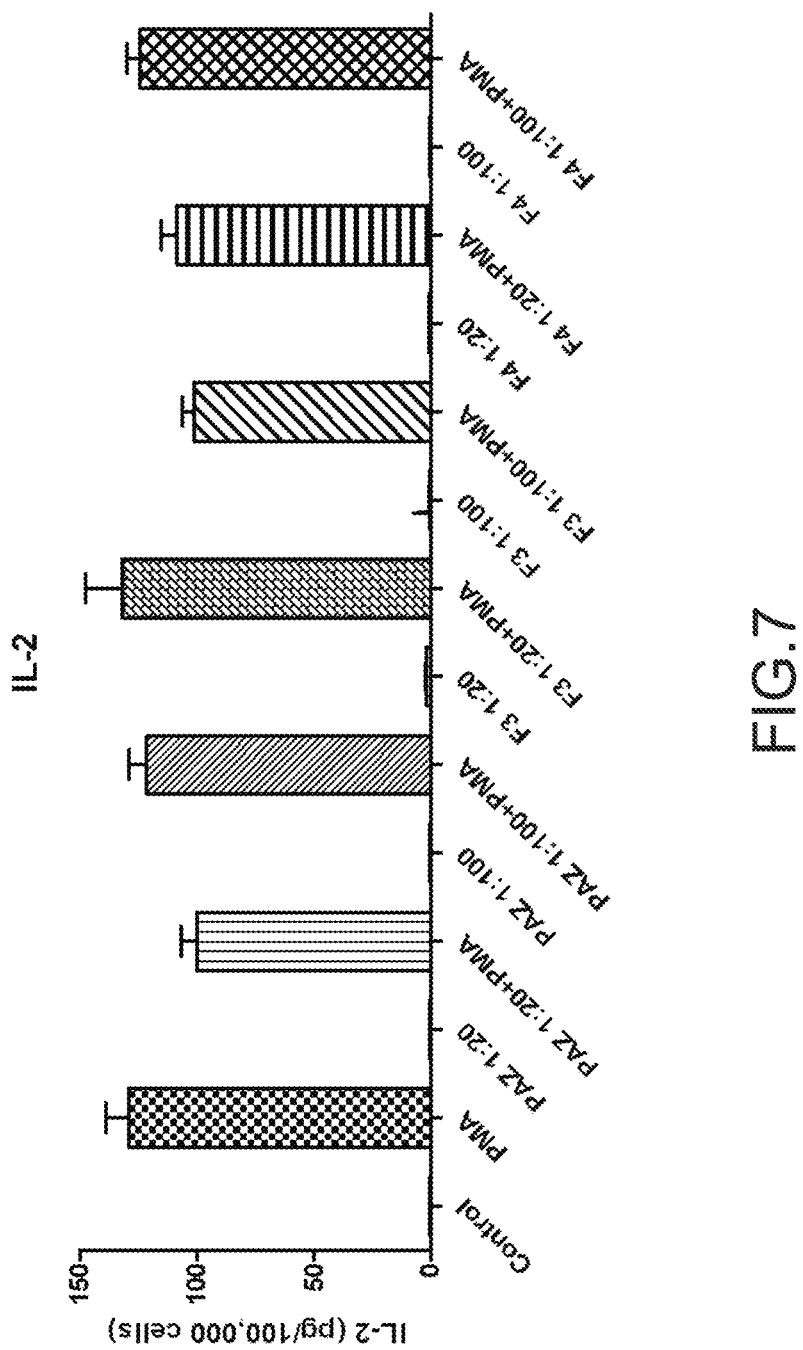
FIG. 7 shows a bar graph illustrating the efficacy of the method on the production of the cytokine IL-2 according to various exemplary embodiments of the present invention.
Figure 8:
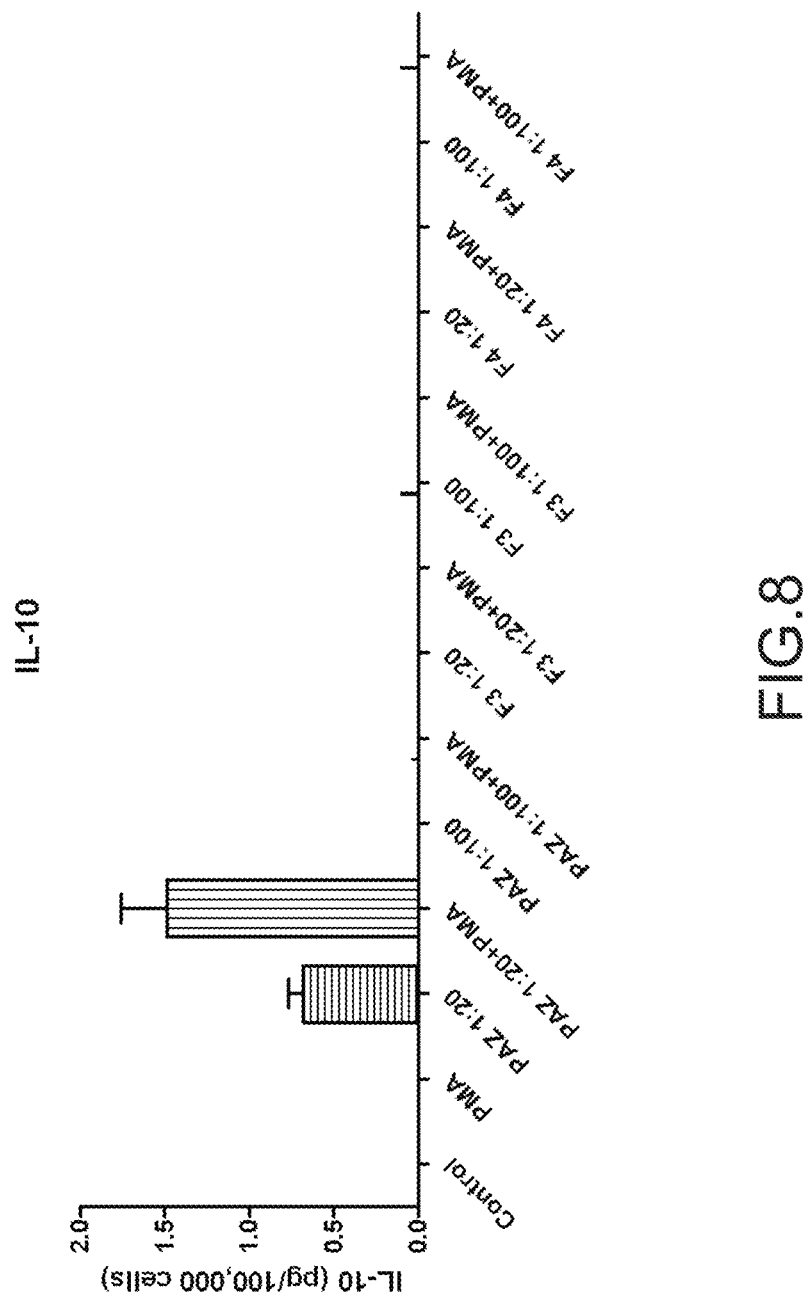
FIG. 8 shows a bar graph illustrating the efficacy of the method on the production of the cytokine IL-10 according to various exemplary embodiments of the present invention.
Figure 9:
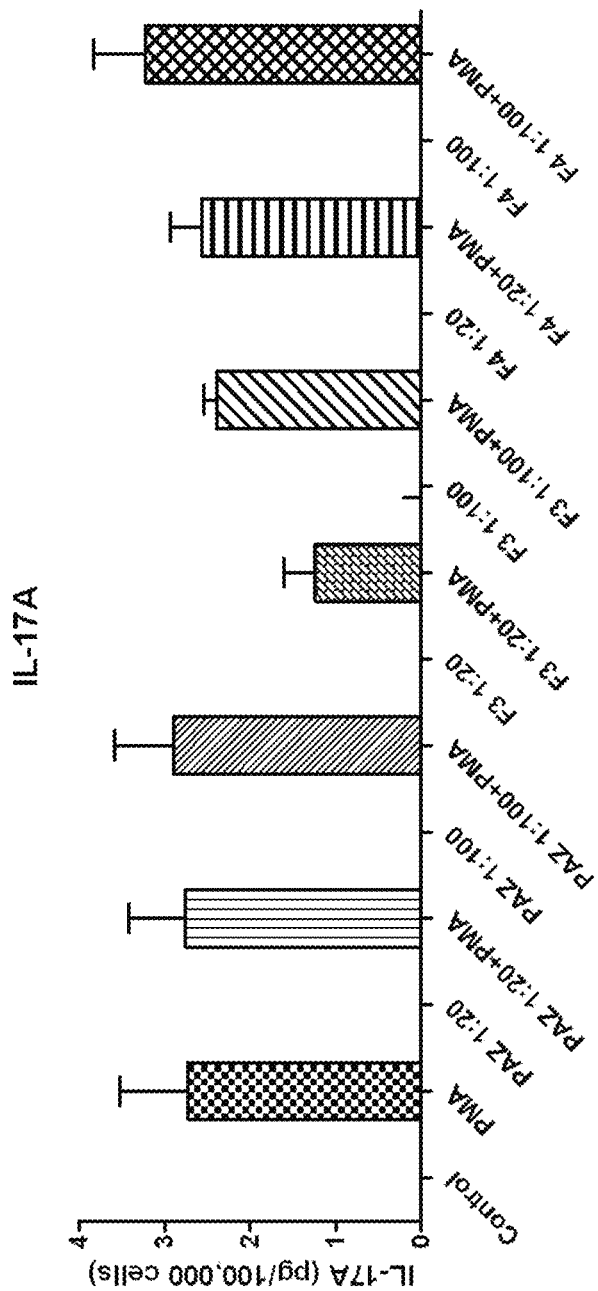
FIG. 9 shows a bar graph illustrating the efficacy of the method on the production of the cytokine IL-17A according to various exemplary embodiments of the present invention.

Turning now to FIGS. 7-9 and in accordance with various exemplary embodiments of the present invention, the effect of phyto-percolate on the production by PBMC of various interleukins is discussed. While certain specific interleukins such as IL-10, and IL-17A are discussed, phyto-percolate also has effects on other interleukins and in other inflammatory pathways.

With particular reference to FIG. 7, the quantity of IL-2 produced (expressed as pg of IL-2/100,000 cells) was measured following the addition of phyto-percolate and various dilutions and fractions thereof to PBMC in the absence of other stimulants, or when added to PBMC treated with PMA, according to one exemplary embodiment of the present invention. As shown, a control consisting of untreated cultured PBMC did not secrete a detectable quantity of IL-2 into the culture medium, whereas additions of PMA to the cultured PBMC resulted in secretion of approximately 125 pg/100,000 cells IL-2. Treatment of cultured PBMC with a 1:20 or 1:100 dilution of phyto-percolate did not induce production of detectable quantities of IL-2 (i.e. approximately the same results as for control, untreated PBMC). The addition of a 1:20 dilution of phyto-percolate, fraction 3 in a 1:100 dilution and fraction 4 in a 1:20 dilution to PBMC stimulated with PMA reduced the production of IL-2 compared to PBMC treated with PMA alone. Treatment of cultured PBMC with fraction 3 and fraction 4, derived from chromatographic fractionation of phyto-percolate, at 1:20 and 1:100 dilutions did not induce production of detectable quantities of IL-2, similar to the control. However, according to this exemplary embodiment, when phyto-percolate in a 1:100 dilution and fraction 3 of phyto-percolate in a 1:20 dilution and fraction 4 of phyto-percolate a 1:100 were tested on PBMC in the presence of PMA, the overall amount of IL-2 did not change significantly when compared with the addition of PMA alone.

Therefore, as depicted in this exemplary embodiment, the addition of phyto-percolate and dilutions, fractions or derivatives thereof may reduce the concentration of IL-2 produced by PBMC in response to agents that stimulate IL-2 production, but they neither do not stimulate the production of IL-2 themselves, nor do they potentiate the production of IL-2 by agents known to induce production of this cytokine (for example PMA). The action of phyto-percolate to reduce (or not to increase) the production of IL-2 by PBMC reflects its ability to reduce the amount of inflammation as well as other effects of IL-2 now known or discovered in the future. According to various exemplary embodiments of the present invention, the ability to not up-regulate an inflammatory cytokine such as IL-2 while simultaneously up-regulating an anti-inflammatory cytokine such as IL-10 is effective at reducing the amount of inflammation and is superior to conventionally available therapies as it reduces undesirable side effects.

Turning now to FIG. 8 and in accordance with yet another exemplary embodiment of the present invention, FIG. 8 depicts the overall production and secretion of IL-10 (expressed as pg of IL-10/100,000 cells) when phyto-percolate, various fractions and dilutions thereof, and PMA are added to cultured PBMC. As shown in FIG. 8, the phyto-percolate in a 1:20 dilution alone and in a 1:20 dilution tested in conjunction with PMA increased the overall secretion of IL-10 compared to control PBMC, which did not secrete detectable quantities of IL-10 into the medium. In this one exemplary embodiment as shown, the various other dilutions and fractions of phyto-percolate alone or in combination with PMA did not appear to effect the overall concentration of IL-10. However, as in the cases with the other exemplary embodiments depicted herein, fractions 3 and 4 comprise only a small percentage of the composition of phyto-percolate and this result does not limit the invention to the point where phyto-percolate in the concentrations and fractions that did not increase IL-10 concentration necessarily cannot ever increase IL-10 concentration.

Therefore, phyto-percolate may increase the overall concentration of IL-10. Increasing the overall concentration of IL-10 should reduce the amount of inflammation as IL-10 is an anti-inflammatory cytokine. Further, the present invention contemplates that the other effects now known or discovered in the future that are attributable to IL-10 can be achieved by the addition of phyto-percolate.

According to various exemplary embodiments of the present invention, phyto-percolate's effects to reduce inflammation can occur due to its effect of reducing the DNA-binding activity of NF-κB, alone or in combination with increasing the production and secretion of anti-inflammatory cytokines such as IL-10 and by reducing inflammatory cytokines such as IL-2 or tumor necrosis factor-alpha ("TNF-α") as noted below. Therefore, the present invention contemplates that phyto-percolate has effects on multiple different cytokines at one time to achieve an overall effect, such as reducing inflammation according to various exemplary embodiments.

With reference now to FIG. 9, and in accordance with one exemplary embodiment of the present invention, the addition of phyto-percolate to a mixture of cultured PBMC to effect the overall production and secretion of IL-17A (expressed as pg of IL-17 secreted/100,000 cells) is disclosed. Besides IL-17A, interleukin 17 (synonymous with interleukin 17A) is similarly affected by the addition of phyto-percolate. As shown, unstimulated cultured control PBMC do not secrete detectable levels of IL-17A whereas the addition of PMA to cultured PBMC resulted in a significant increase of IL-17A to approximately 3 pg/100,000 cells. The addition of phyto-percolate in a 1:20 dilution or a 1:100 dilution did not result in detectable secretion of IL-17A from control PBMC, and the addition of 1:20 dilution or a 1:100 dilution of phyto-percolate or fraction 4 in a 1:100 dilution in the presence of PMA did not cause any change in the levels of IL-17A secreted in response to PMA alone. Fraction 3 and fraction 4 of phyto-percolate in both 1:20 dilution and 1:100 dilution did not result in detectable secretion of IL-17A from control PBMC. An addition of fraction 3 of phyto-percolate in a 1:20 dilution significantly reduced the secretion of IL-17A by PBMC in response to PMA treatment to approximately 1 pg/100,000 cells. Fraction 3 of phyto-percolate in a 1:100 dilution as well as fraction 4 of phyto-percolate in a 1:20 dilution also reduced the section of IL-17A by PBMC in response to PMA treatment as shown.

Figure 10:
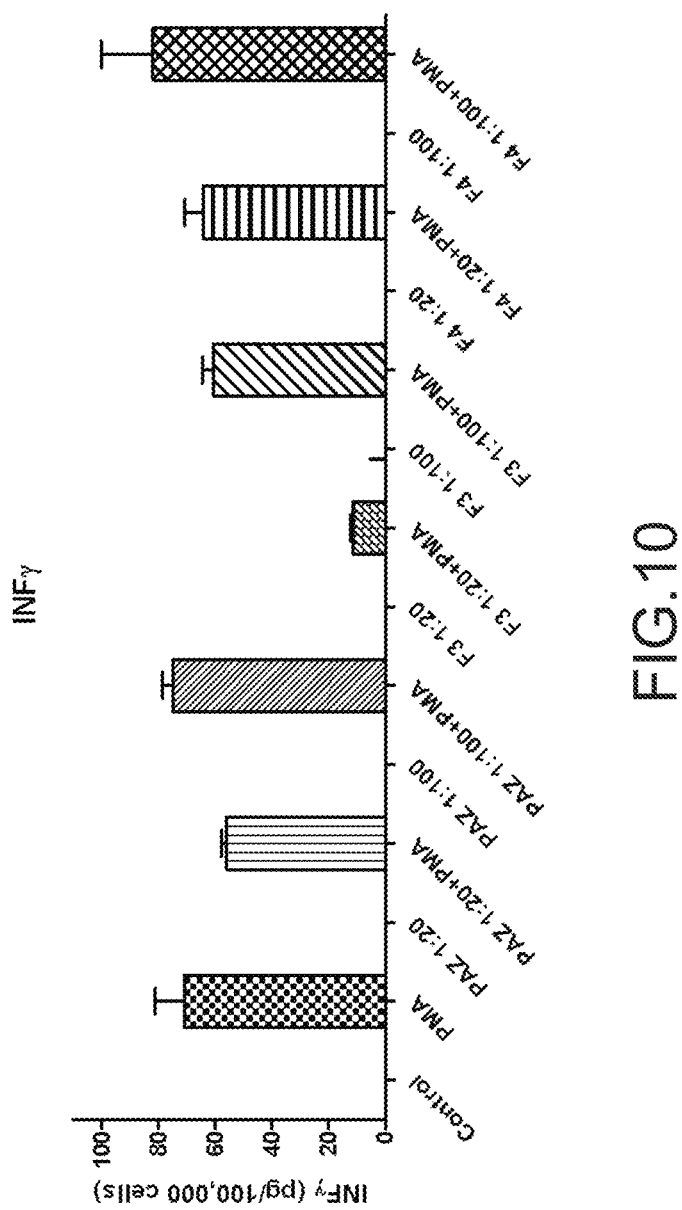
FIG. 10 shows a bar graph illustrating the efficacy of the method on the production of the cytokine INF-γ according to various exemplary embodiments of the present invention.
Figure 11:
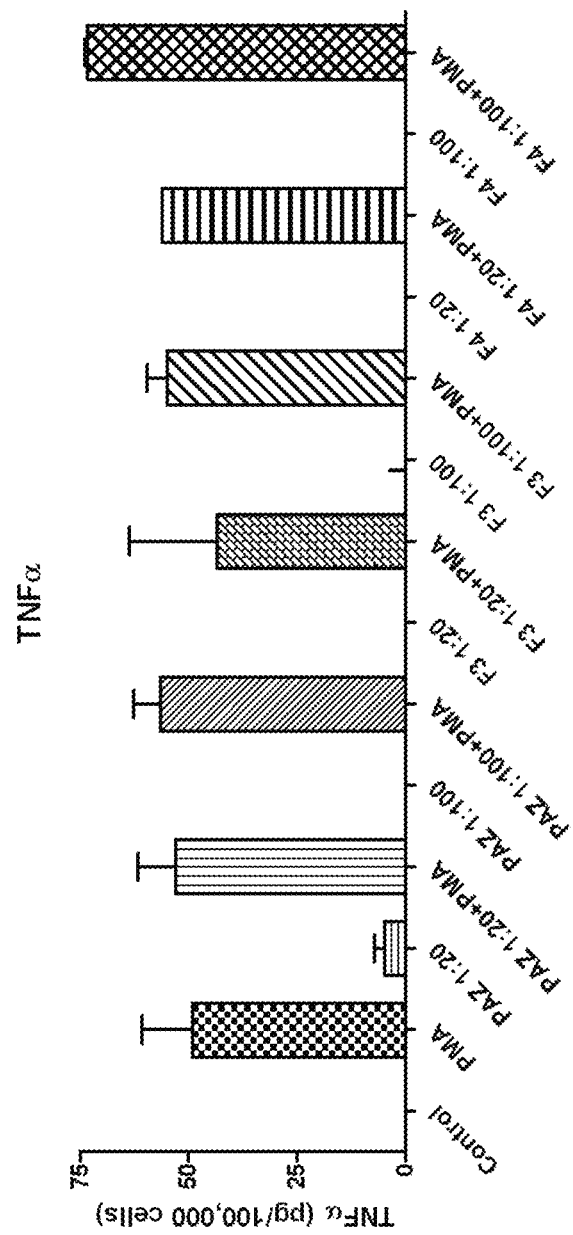
FIG. 11 shows a bar graph illustrating the efficacy of the method on the production of the cytokine TNF-α according to various exemplary embodiments of the present invention.

With reference to FIGS. 10-11, the effect of phyto-percolate on other cytokines is disclosed. Specifically, the effect of phyto-percolate in various dilutions and fractions on interferon-gamma (IFN-γ), tumor necrosis factor-alpha (TNF-α), and granulocyte macrophage colony stimulating factor (GM-CSF) is disclosed.

Figure 12:
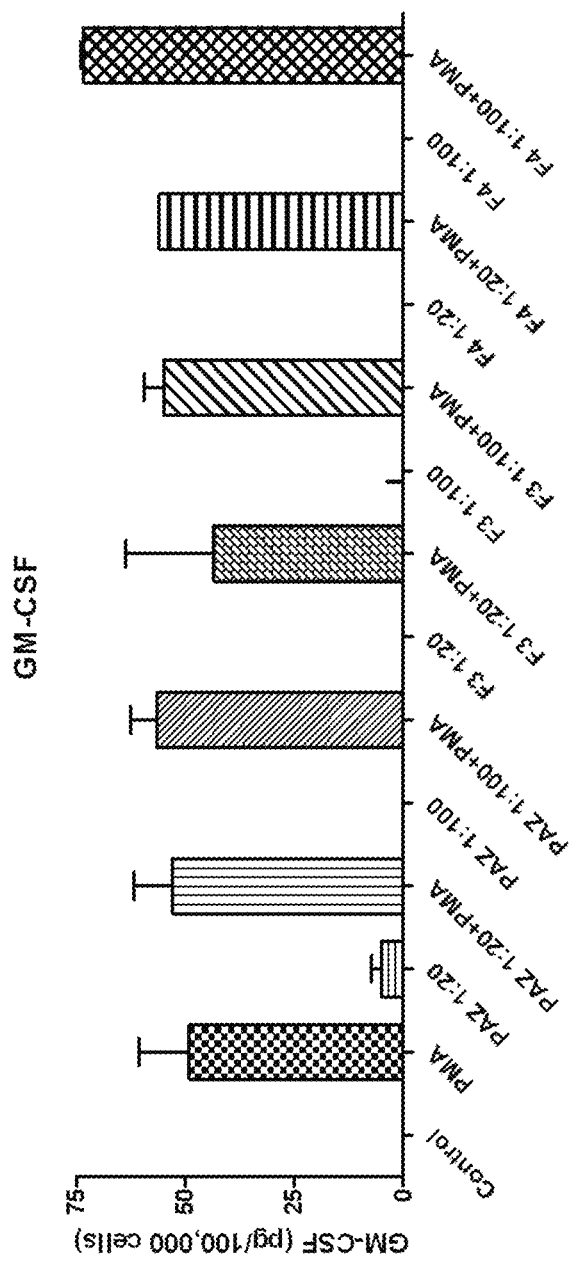
FIG. 12 shows a bar graph illustrating the efficacy of the method on the production of GM-CSF according to various exemplary embodiments of the present invention.

As shown in FIG. 12, and in accordance with one exemplary embodiment of the present invention, the effect of phyto-percolate on the concentration of IFN-γ (expressed as pg of IFN-γ secreted/100,000 cells) is disclosed. According to this exemplary embodiment, unstimulated cultured control PBMC do not secrete detectable levels of IFN-γ whereas the addition of PMA to cultured PBMC resulted in significant secretion of IFN-γ to approximately 70 pg/100,000 cells. While the addition of phyto-percolate to cultured PBMC in a dilution of 1:20, a dilution of 1:100, or fraction 3 or fraction 4 in these dilutions did not result in the secretion of detectable levels of IFN-γ in this exemplary embodiment, the addition of phyto-percolate in a dilutions of 1:20 to PBMC in combination with PMA decreased the overall secretion of IFN-γ that is induced by PMA alone. The addition of fraction 3 of phyto-percolate in a 1:20 dilution significantly decreased the PMA-induced secretion of IFN-γ to approximately 10 pg. Fraction 3 of phyto-percolate in a 1:100 dilution decreased the PMA-induced secretion of IFN-γ to approximately 60 pg as did fraction 4 of phyto-percolate in a 1:20 dilution.

Therefore, phyto-percolate does not induce the production of IFN-γ and may modulate the overall production of IFN-γ caused by other agents and thus enable the benefits that may be derived therefrom.

With reference now to FIG. 11 and in accordance with an exemplary embodiment of the present invention, effect of phyto-percolate on the production and secretion of TNF-α (expressed as pg secreted/100,000 cells) was measured. According to this exemplary embodiment, unstimulated cultured control PBMC do not secrete detectable levels of TNF-α whereas the addition of PMA to cultured PBMC resulted in significant secretion of TNF-α to approximately 50 pg/100,000 cells. The phyto-percolate in a 1:100 dilution or fraction 3 in a 1:20 or 1:100 dilution or fraction 4 of phyto-percolate in a 1:20 or 1:100 dilution do not induce the secretion of detectable levels of TNF-α. Phyto-percolate and fractions derived therefrom did not significantly alter the PMA-induced secretion of TNF-α by cultured PBMC.

Turning now to FIG. 12 and in accordance with another exemplary embodiment of the present invention, the effect of administering various concentrations and fractions of phyto-percolate on the production and secretion of GM-CSF by PBMC (expressed as pg secreted/100,000 cells) is discussed. As shown, a control consisting of unstimulated cultured PBMC did not produce a measurable amount of GM-CSF, whereas the addition of PMA induced the secretion of approximately 50 pg/100,000 cells. Phyto-percolate in a 1:20 dilution induced the secretion of a very low level GM-CSF (approximately 5 pg/100,000 cells) whereas a 1:00 dilution of phyto-percolate or various dilutions of fractions 3 and 4 did not induce GMCSF secretion. Further, phyto-percolate as well as fraction 3 in both a 1:20 dilution and a 1:100 dilutions and fraction 4 at 1:20 dilution did not influence the production of GM-CSF by PBMC in the presence of PMA.

Therefore, according to these exemplary embodiments, phyto-percolate by itself in various dilutions and fractions does not cause the secretion of appreciable quantities of GM-CSF and phyto-percolate in various dilutions and fractions does not significantly alter the production of GM-CSF that is induced as the result of treatment by other agents.

Therefore, according to various exemplary embodiments of the present invention, the administration of phyto-percolate regulates various cytokines and NF-κB to achieve certain desired effects such as the reduction of inflammation. Unlike compositions of the prior art, phyto-percolate can regulate multiple cytokines to achieve reduced inflammation. For example, as shown and discussed above, the administration of phyto-percolate can up-regulate IL-10 without up-regulating IL-2 to greater reduce inflammation.

Further, phyto-percolate and various dilutions and fractions thereof are capable of inhibiting NF-κB and TNF-α induced activation of NF-κB thus indicating that phyto-percolate functions as an antioxidant. Also, according to certain exemplary embodiments, administering phyto-percolate in various dilutions and fractions, especially fraction 3, significantly inhibits the DNA-binding activity of NF-κB. Administering an effective amount of phyto-percolate will not induce certain pro-inflammatory cytokines such as TNF-α or IFN-γ, while inducing various anti-inflammatory cytokines such as IL-10, to reduce inflammation. Further, according to these various exemplary embodiments, the administration of phyto-percolate did not have a toxic or irritant effect on cells or tissue.

In certainly exemplary embodiments, the methods described herein can be used to treat animals. For example, mastitis in a cow can be treated by administering a therapeutically effective amount of one or more isolates or fractions of phyto-percolate derived from culturing microorganisms of ATCC Deposit No. PTA-5863.

What is claimed is:

1. A method of treating inflammation in a subject in need thereof; the method comprising administering to said subject an effective amount of phyto-percolate derived from culturing microorganisms of ATCC Deposit #PTA-5863 wherein the inflammation is treated by the phyto-percolate up regulating anti-inflammatory cytokines while down regulating pro-inflammatory cytokines.

2. The method of claim 1, wherein the anti-inflammatory cytokines comprise IL-10 and the inflammatory cytokines comprise IL-2.

3. The method of claim 1, wherein the inflammatory cytokines comprise TNF-α.

4. The method of claim 1, wherein the inflammatory cytokines comprise IFN-γ.

5. The method of claim 1, wherein the anti-inflammatory cytokines comprise IL-10 and the inflammatory cytokines comprise IL-2, TNF-α, and IFN-γ.

6. The method of claim 1, wherein the phyto-percolate affects the expression of cytokines on a cellular level.

7. The method of claim 1, wherein the phyto-percolate further affects the activation of NF-κB.

8. A method of affecting NF-κB in a subject in need thereof; said method comprising administering to said subject an effective amount of phyto-percolate derived from culturing microorganisms of ATCC Deposit #PTA-5863 to reduce the overall amount of NF-κB.

9. The method of claim 8, wherein the affecting of NF-κB occurs by decreasing expression, activation or the DNA-binding activity of NF-κB.

10. The method of claim 8, wherein the affecting of NF-κB reduces inflammation.

11. The method of claim 8, wherein the affecting of NF-κB results in affecting various viruses.

12. The method of claim 11, wherein the viruses comprise the HIV virus.

13. The method of claim 8, wherein the affecting of NF-κB treats disorders of the immune system, including cancer.

14. The method of claim 8, wherein the affecting of NF-κB affects host immune response.

15. A method of affecting cytokines in a subject in need thereof; said method comprising administering to said subject an effective amount of phyto-percolate derived from culturing microorganisms of ATCC Deposit #PTA-5863 to selectively target and up regulate certain cytokines while down regulating other cytokines to have a specific effect that is achieved by the up regulation and down regulation of various cytokines.

16. The method of claim 15, wherein the cytokines affected comprise interleukins.

17. The method of claim 15, wherein the cytokines affected comprise TNF-α.

18. The method of claim 15, wherein the cytokines affected comprise IL-2, IL-10, IL-17A, and IL-17 and the affecting of the IL-2, IL-10, IL-17A, and IL-17 results in the regulation of the immune response.

19. A method of treating mastitis in a cow, said method comprising administering to said subject to said cow a therapeutically effective amount of one or more isolates or fractions of phyto-percolate derived from culturing microorganisms of ATCC Deposit No. PTA-5863.

* * * * *